(12) United States Patent
Stewart et al.

(10) Patent No.: US 7,485,092 B1
(45) Date of Patent: Feb. 3, 2009

(54) VESSEL HARVESTING APPARATUS AND METHOD

(75) Inventors: Michael C Stewart, San Jose, CA (US); Liming Lau, Palo Alto, CA (US); Michael Wei, San Mateo, CA (US); John P Lunsford, San Carlos, CA (US); Albert K Chin, Palo Alto, CA (US); Peter Tachi Callas, Redwood City, CA (US); Benjamin Sherman, Milpitas, CA (US)

(73) Assignee: Maquet Cardiovascular LLC, San Jose, CA (US)

( * ) Notice: Subject to any disclaimer, the term of this patent is extended or adjusted under 35 U.S.C. 154(b) by 573 days.

(21) Appl. No.: 10/054,477

(22) Filed: Jan. 18, 2002

Related U.S. Application Data

(63) Continuation-in-part of application No. 09/413,012, filed on Oct. 5, 1999, which is a continuation of application No. 09/133,136, filed on Aug. 12, 1998.

(51) Int. Cl.
*A61B 1/00* (2006.01)
(52) U.S. Cl. .................. 600/127; 600/104; 600/114; 600/129; 600/176; 604/104; 604/105; 604/106; 604/107; 604/108; 606/190; 606/191
(58) Field of Classification Search ........... 600/114, 600/129, 176, 183; 606/190–191
See application file for complete search history.

(56) References Cited

U.S. PATENT DOCUMENTS

| | | |
|---|---|---|
| 2,004,559 A | 6/1935 | Wappler et al. |
| 2,028,635 A | 1/1936 | Wappler |
| 2,031,682 A | 2/1936 | Wappler et al. |
| 3,200,028 A | 8/1965 | Chisolm |
| 3,354,478 A | 11/1967 | Allen |
| 3,391,690 A | 7/1968 | Armao |
| 3,439,523 A | 4/1969 | Wood |
| 3,613,682 A | 10/1971 | Naylor |
| 3,625,202 A | 12/1971 | Oyoshirhara et al. |
| 3,772,127 A | 11/1973 | James |
| 3,929,137 A | 12/1975 | Gonser |
| 3,934,115 A | 1/1976 | Peterson |
| 3,938,527 A | 2/1976 | Rioux et al. |
| 4,030,743 A | 6/1977 | Warthen |
| 4,031,898 A | 6/1977 | Hiltebrandt et al. |
| 4,196,734 A | 4/1980 | Harris |
| 4,213,460 A | 7/1980 | Weiner |
| 4,285,753 A | 8/1981 | Warthen |
| 4,315,510 A | 2/1982 | Kihn |

(Continued)

FOREIGN PATENT DOCUMENTS

DE        H24669        10/1956

(Continued)

*Primary Examiner*—Linda C Dvorak
*Assistant Examiner*—Matthew J Kasztejna
(74) *Attorney, Agent, or Firm*—Fenwick & West LLP

(57) ABSTRACT

Apparatus and method for harvesting selected vessels in the body of a patient include manual manipulation of a rigid dissecting endoscope and the reconfiguration thereof to facilitate tissue dissection and tissue dilation in the formation of an anatomical space about the vessel within which side-branch vessels may be manipulated in preparation for severance and removal of the vessel from the anatomical space.

3 Claims, 22 Drawing Sheets

U.S. PATENT DOCUMENTS

| | | | |
|---|---|---|---|
| 4,359,052 A | 11/1982 | Staub | |
| 4,370,980 A | 2/1983 | Lottick | |
| 4,493,320 A | 1/1985 | Treat | |
| 4,516,574 A | 5/1985 | Hewes, Jr. | |
| 4,597,379 A | 7/1986 | Kihn et al. | |
| 4,655,216 A | 4/1987 | Tischer | |
| 4,662,068 A | 5/1987 | Polonsky | |
| 4,671,274 A | 6/1987 | Sorochenko | |
| 4,705,041 A * | 11/1987 | Kim, II | 606/108 |
| 4,931,042 A | 6/1990 | Holmes et al. | |
| 4,979,771 A | 12/1990 | Childs, III | |
| 4,985,030 A | 1/1991 | Melzer et al. | |
| 5,046,251 A | 9/1991 | Scott | |
| 5,122,137 A | 6/1992 | Lennox | |
| 5,139,508 A | 8/1992 | Kantrowitz et al. | |
| 5,147,356 A | 9/1992 | Bhatta | |
| 5,151,102 A | 9/1992 | Kamiyama et al. | |
| 5,171,255 A | 12/1992 | Rydell | |
| 5,190,541 A | 3/1993 | Abele et al. | |
| 5,192,280 A | 3/1993 | Parins | |
| 5,197,649 A | 3/1993 | Bessler et al. | |
| 5,203,773 A | 4/1993 | Green | |
| 5,207,691 A | 5/1993 | Nardella | |
| 5,217,458 A | 6/1993 | Parins | |
| 5,226,890 A | 7/1993 | Ianniruberto et al. | |
| 5,226,908 A | 7/1993 | Yoon | |
| 5,250,046 A | 10/1993 | Lee | |
| 5,258,006 A | 11/1993 | Rydell et al. | |
| 5,267,998 A | 12/1993 | Hagen | |
| 5,276,306 A | 1/1994 | Huffman | |
| 5,290,249 A | 3/1994 | Foster et al. | |
| 5,290,286 A | 3/1994 | Parins | |
| 5,330,497 A | 7/1994 | Freitas et al. | |
| 5,336,221 A | 8/1994 | Anderson | |
| 5,336,229 A | 8/1994 | Noda | |
| 5,352,222 A | 10/1994 | Rydell | |
| 5,360,428 A | 11/1994 | Hutchinson, Jr. | |
| 5,376,087 A | 12/1994 | Haber et al. | |
| 5,389,098 A | 2/1995 | Tsuruta et al. | |
| 5,401,273 A | 3/1995 | Shippert | |
| 5,403,312 A | 4/1995 | Yates et al. | |
| 5,411,508 A | 5/1995 | Bessler et al. | |
| 5,443,463 A | 8/1995 | Stern et al. | |
| 5,445,638 A | 8/1995 | Rydell et al. | |
| 5,447,502 A | 9/1995 | Haaga | |
| 5,451,223 A | 9/1995 | Ben-Simhon | |
| 5,452,513 A | 9/1995 | Zinnbauer et al. | |
| 5,458,598 A | 10/1995 | Feinberg et al. | |
| 5,480,409 A | 1/1996 | Riza | |
| 5,496,317 A | 3/1996 | Goble et al. | |
| 5,512,721 A | 4/1996 | Young et al. | |
| 5,514,236 A | 5/1996 | Avellanet et al. | |
| 5,527,331 A | 6/1996 | Kresch et al. | |
| 5,556,563 A | 9/1996 | von der Heyde et al. | |
| 5,565,122 A | 10/1996 | Zinnbauer et al. | |
| 5,582,611 A | 12/1996 | Tsuruta et al. | |
| 5,591,183 A | 1/1997 | Chin | |
| 5,595,565 A | 1/1997 | Treat et al. | |
| 5,601,601 A | 2/1997 | Tal et al. | |
| 5,603,698 A * | 2/1997 | Roberts et al. | 604/104 |
| 5,647,871 A | 7/1997 | Levine et al. | |
| 5,665,085 A | 9/1997 | Nardella | |
| 5,688,270 A | 11/1997 | Yates et al. | |
| 5,688,286 A | 11/1997 | Yoon | |
| 5,690,847 A | 11/1997 | LaValley et al. | |
| 5,693,051 A | 12/1997 | Schulze et al. | |
| 5,707,382 A | 1/1998 | Sierocuk et al. | |
| 5,709,680 A | 1/1998 | Yates et al. | |
| 5,725,479 A * | 3/1998 | Knight et al. | 600/210 |
| 5,730,756 A * | 3/1998 | Kieturakis et al. | 606/190 |
| 5,735,848 A | 4/1998 | Yates et al. | |
| 5,755,717 A | 5/1998 | Yates et al. | |
| 5,776,112 A * | 7/1998 | Stephens et al. | 604/264 |
| 5,797,907 A | 8/1998 | Clement | |
| 5,807,393 A | 9/1998 | Williamson, IV et al. | |
| 5,810,811 A | 9/1998 | Yates et al. | |
| 5,817,061 A | 10/1998 | Goodwin et al. | |
| 5,817,062 A | 10/1998 | Flom et al. | |
| 5,827,279 A | 10/1998 | Hughett et al. | |
| 5,827,281 A | 10/1998 | Levin | |
| 5,843,017 A | 12/1998 | Yoon | |
| 5,868,785 A | 2/1999 | Tal et al. | |
| 5,871,498 A * | 2/1999 | Jervis et al. | 606/192 |
| 5,914,062 A | 6/1999 | von der Heyde | |
| 6,077,277 A | 6/2000 | Mollenauer et al. | |
| H1904 H | 10/2000 | Yates et al. | |
| 6,287,304 B1 | 9/2001 | Eggers et al. | |
| 6,432,115 B1 | 8/2002 | Mollenauer et al. | |
| 6,544,260 B1 | 4/2003 | Markel et al. | |
| 2004/0102804 A1 | 5/2004 | Chin | |

FOREIGN PATENT DOCUMENTS

| | | |
|---|---|---|
| DE | 2550693 | 5/1977 |
| DE | 3002088 | 7/1981 |
| DE | 40469 | 8/1987 |
| EP | 0517244 A1 | 12/1992 |
| EP | 0517244 B1 | 3/1996 |
| EP | 0518230 B1 | 5/1996 |
| SU | 639545 | 12/1978 |
| SU | 1498474 | 8/1989 |
| WO | WO 92/08513 | 5/1992 |
| WO | WO 93/08754 | 5/1993 |
| WO | WO 94/24949 | 11/1994 |
| WO | WO 94/24951 | 11/1994 |
| WO | WO 98/38935 | 9/1998 |

* cited by examiner

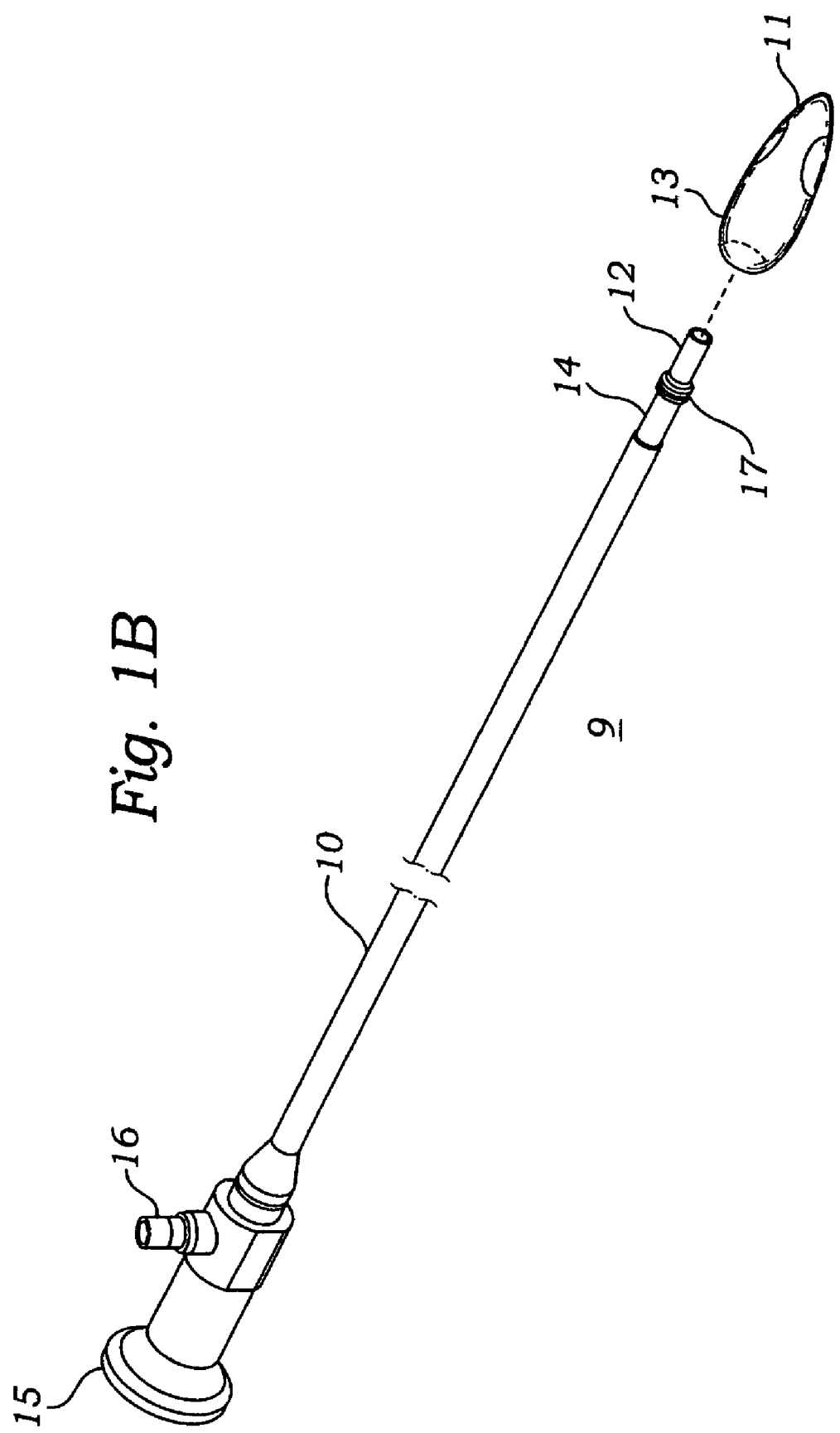

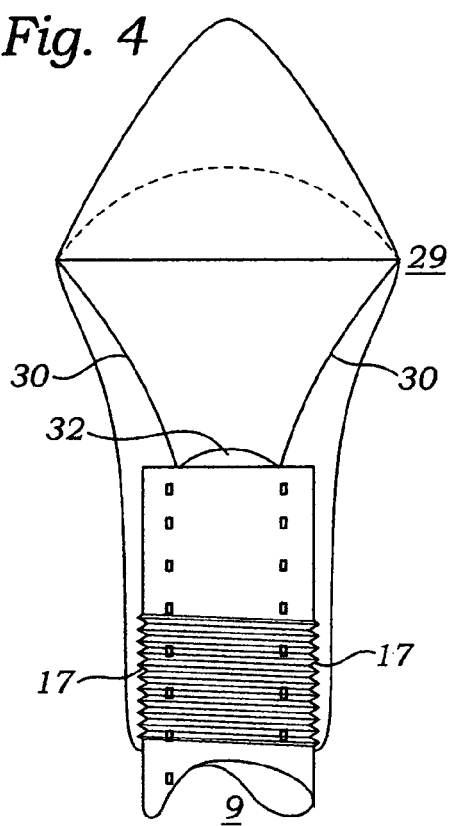
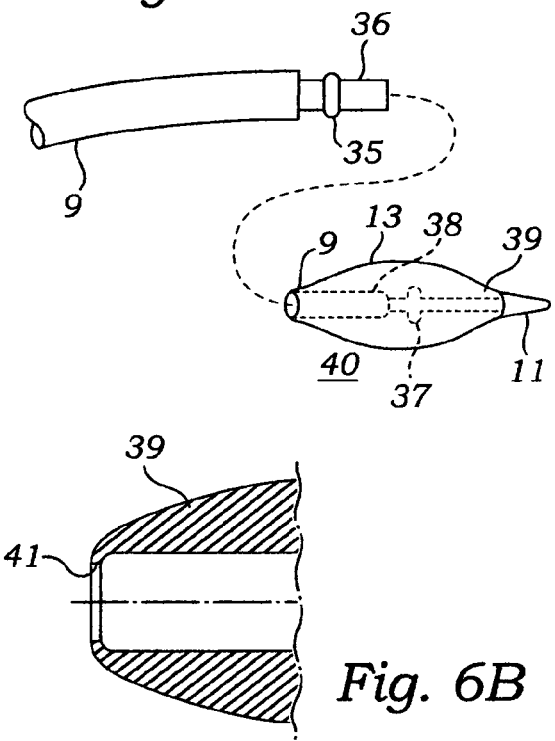
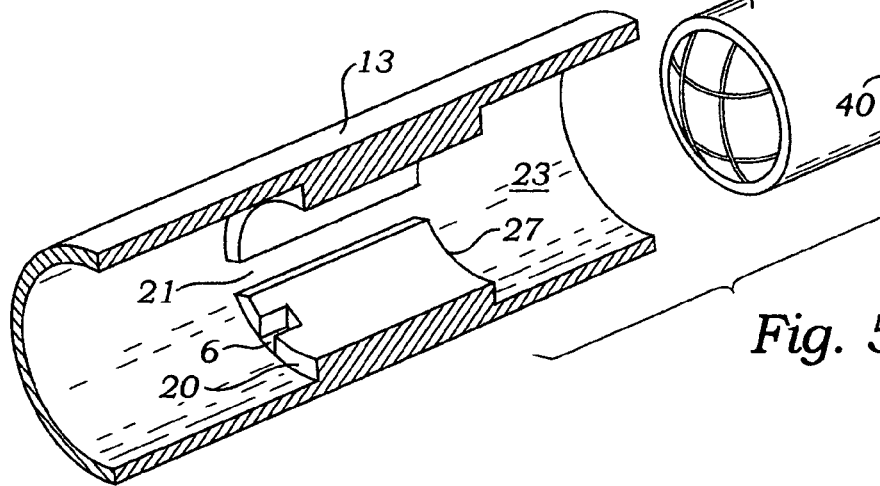

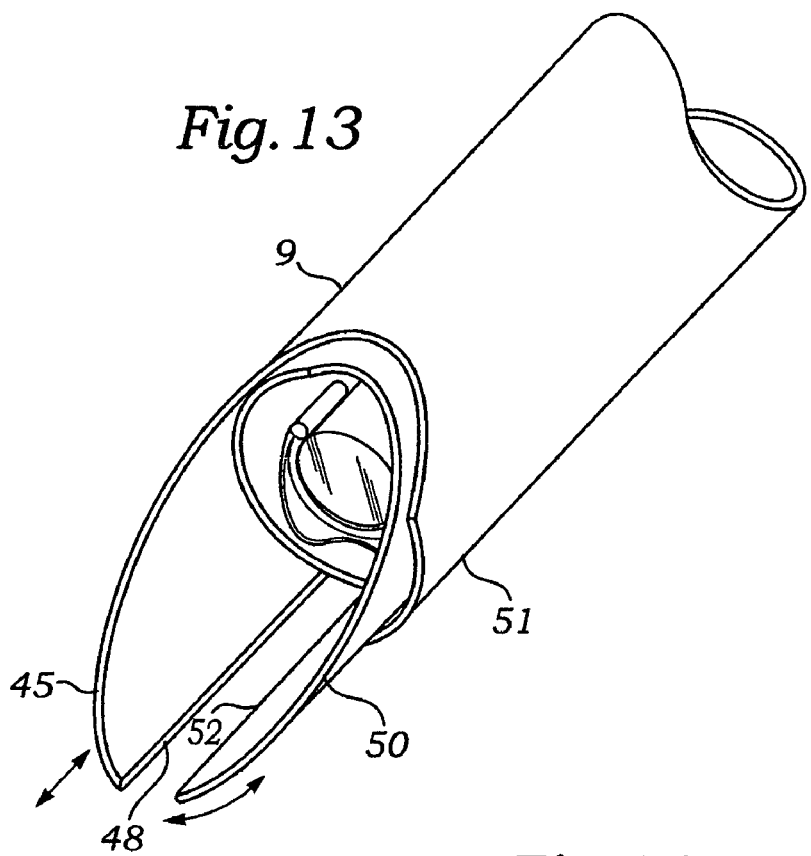
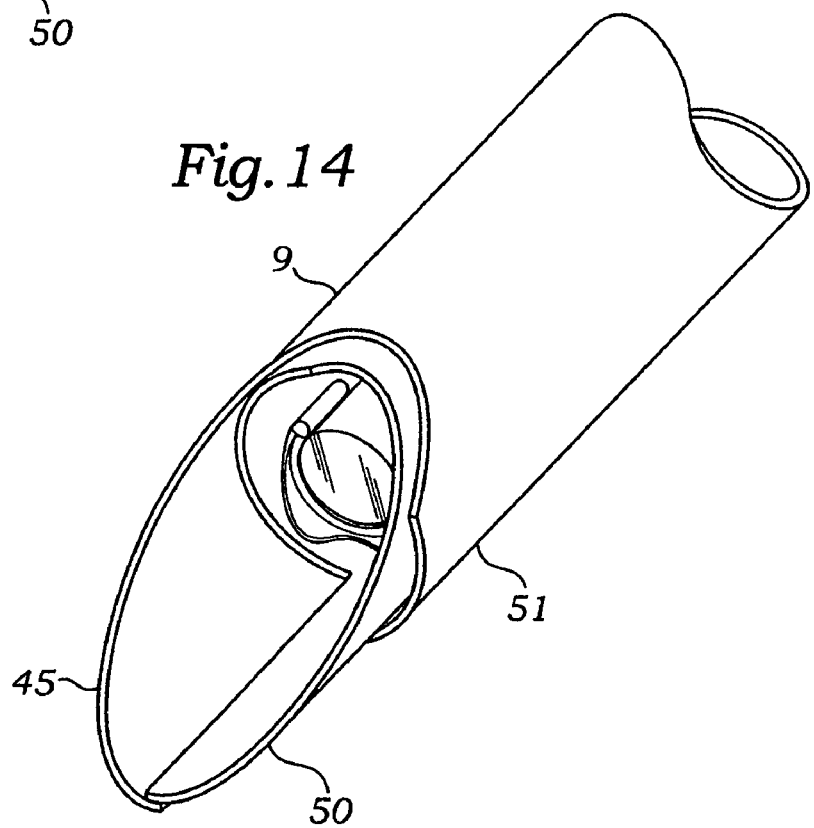

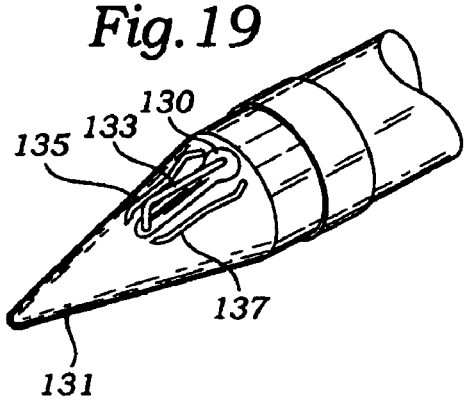
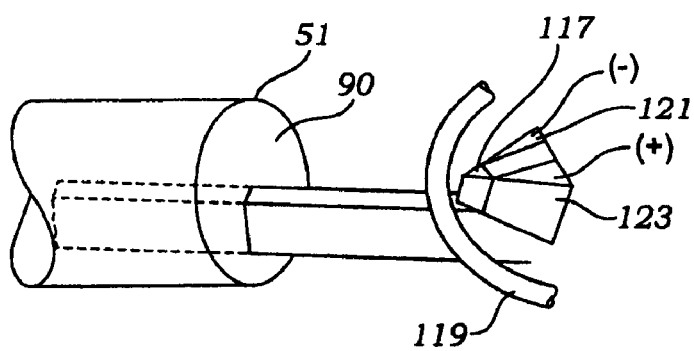
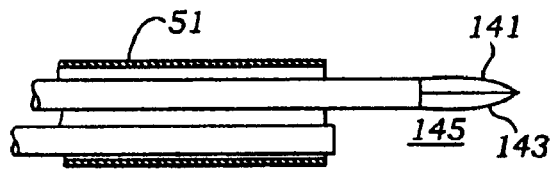
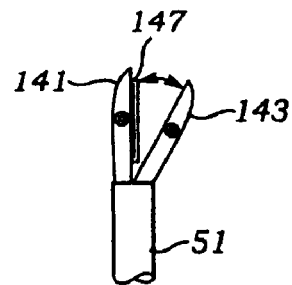
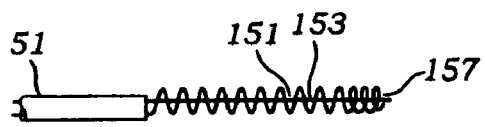
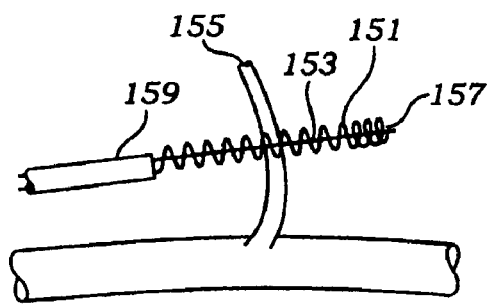

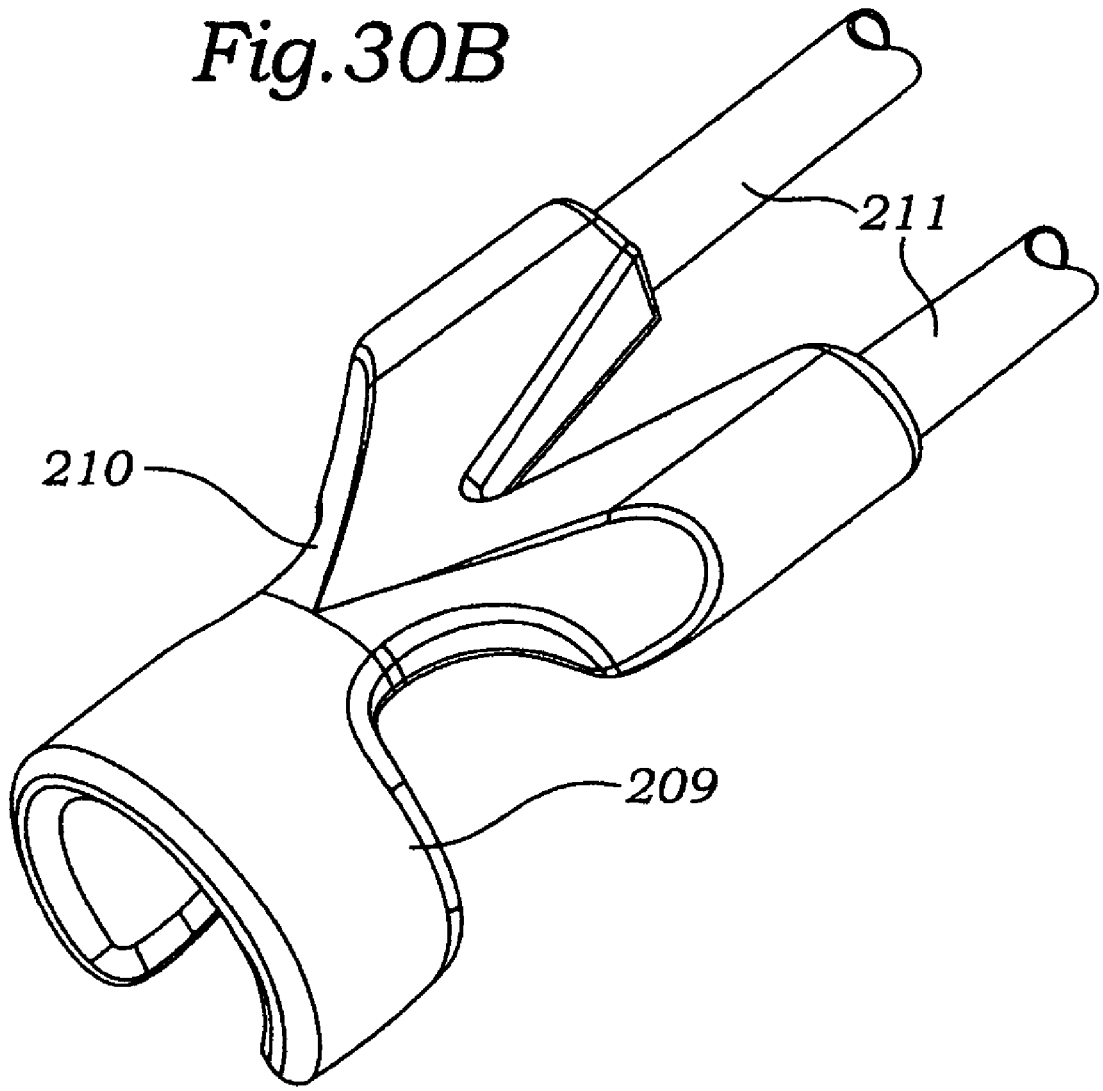

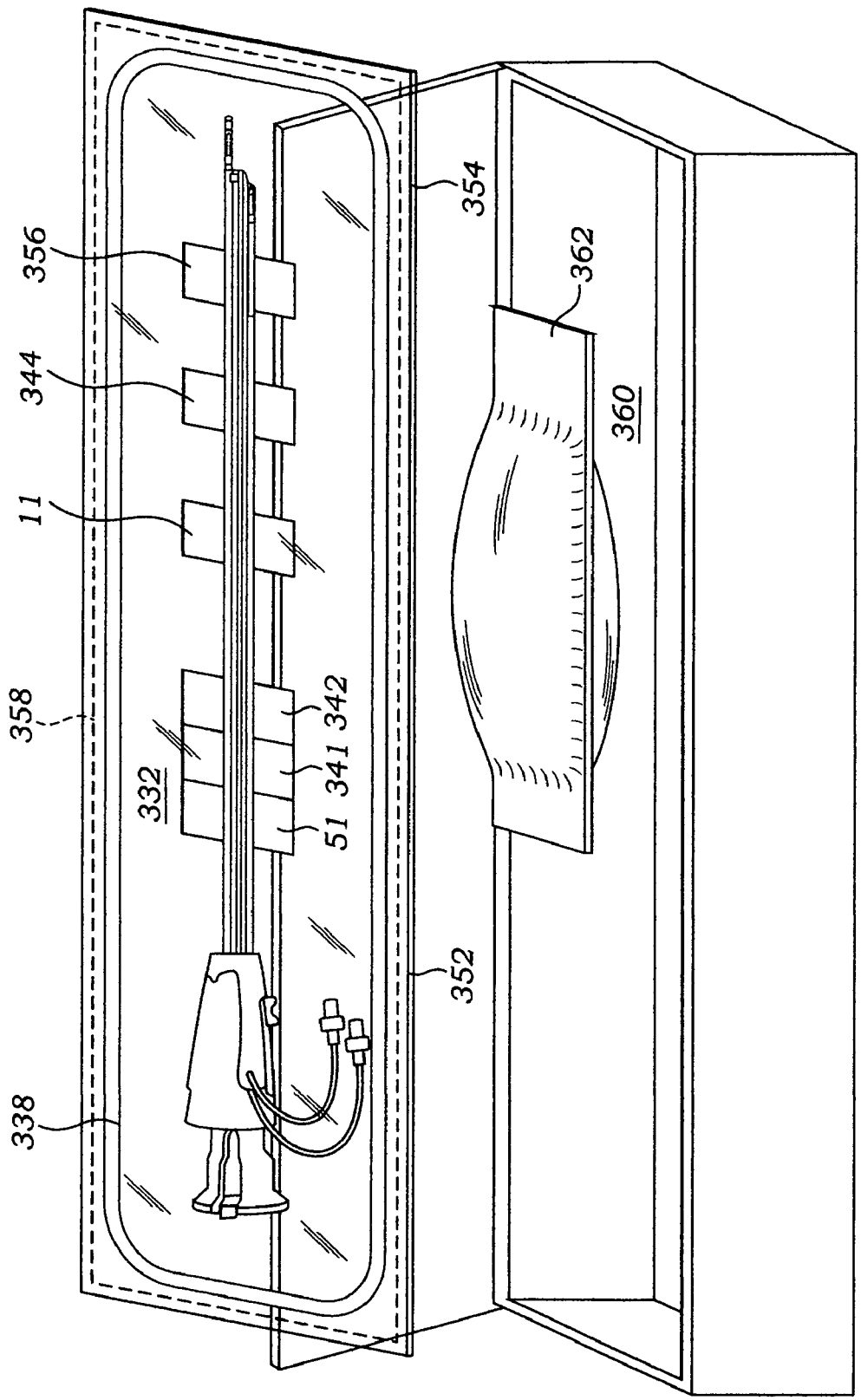

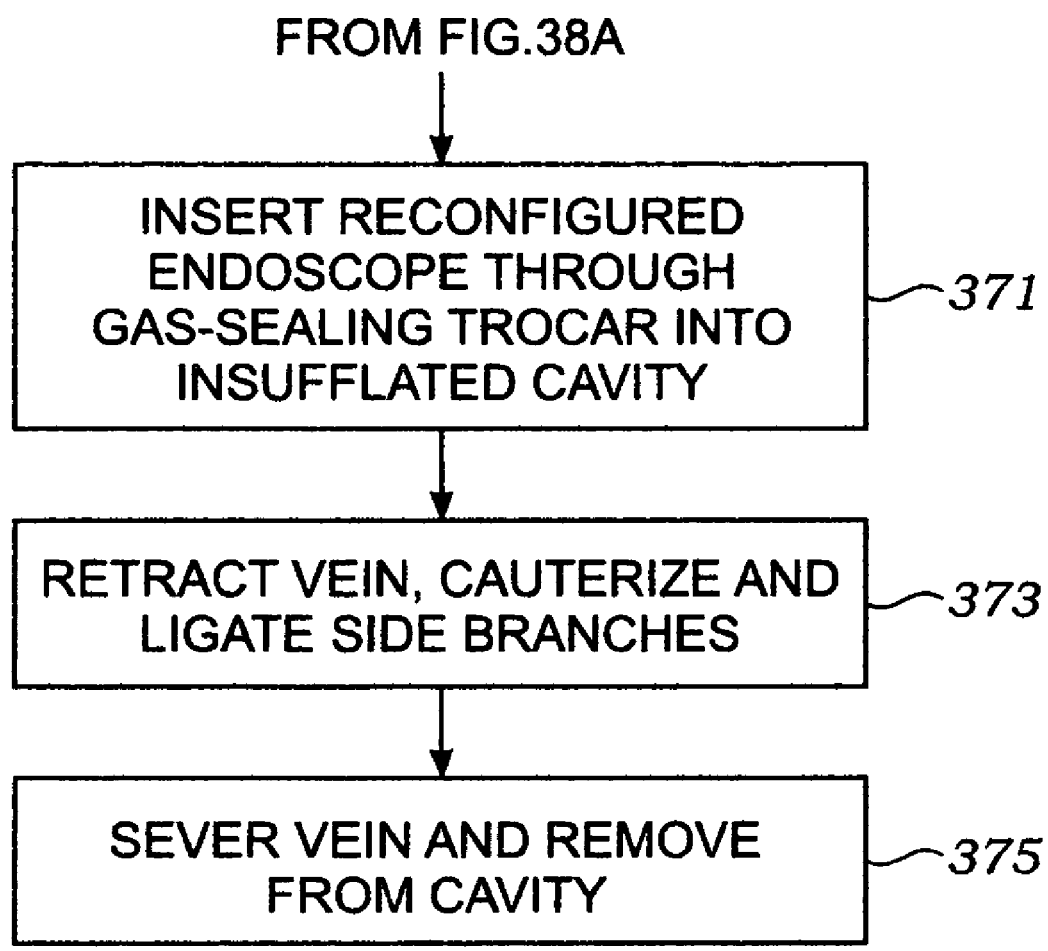

VESSEL HARVESTING APPARATUS AND METHOD

RELATED APPLICATIONS

This application is a continuation-in-part of pending U.S. patent application Ser. No. 09/413,012 filed on Oct. 5, 1999, which is a continuation of pending U.S. patent application Ser. No. 09/133,136 filed on Aug. 12, 1998, and the subject matter of this application relates to the subject matters described in U.S. Pat. No. 6,176,825 issued on Jan. 23, 2001 and in U.S. Pat. No. 5,980,549 issued on Nov. 9, 1999, and in pending U.S. patent application Ser. No. 09/614,482 filed on Jul. 10, 2000, which subject matters are incorporated herein by these references.

FIELD OF THE INVENTION

This invention relates to surgical instruments and procedures for subcutaneously harvesting blood vessels particularly for use in coronary bypass surgery.

BACKGROUND OF THE INVENTION

Contemporary coronary bypass surgery commonly entails grafting a segment of a patient's own blood vessel around a stenosis or other anomaly in a coronary artery to improve circulation in regions of the cardiac muscle adversely affected by diminished blood flow past such stenosis or anomaly. The bypass or shunting vessel is commonly prepared from the patient's saphenous vein or radial artery, and minimally invasive techniques are now routinely employed to harvest a segment of such vein using subcutaneous surgical instruments and procedures that dissect the saphenous vein from connective tissue to promote convenient harvesting of the vessel with minimal cutaneous incision.

Specifically, common surgical practices for harvesting the saphenous vein include making a small incision over the vein near the knee to expose the vein and facilitate introduction of an elongated tissue dissector to dissect connective tissue from the vein along its course in either or both directions from the incision near the knee. The saphenous vein may thus be separated from surrounding connecting tissue, and the anatomical space or cavity thus formed along the course of the vessel may be maintained open under insufflation of the cavity to facilitate operation on the vein. To implement such maintenance of a working space about the vessel being harvested, an access port with a sliding gas seal may be installed in the initial incision and endoscopic instruments may be passed through the seal and manipulated to harvest the vessel from within the cavity which is expanded by gas supplied thereto under pressure. Lateral or side branches of the vessel may be cauterized or otherwise ligated and transected to free the saphenous vein from anatomical attachments and then severed near extreme ends of the cavity for removal from the body, for example, through the initial incision.

Current systems commonly employ a balloon coupled to the cannula for intermittent inflation and deflation to enlarge the surgical cavity as the cannula is advanced. However, use of a balloon to enlarge surgical cavities has the disadvantage that multiple balloon inflation and deflation tires the surgeon's hands, and makes it difficult to retain the precise hand control needed to perform the surgical procedure.

In such vessel harvesting procedure, it is highly desirable to have visualization of the vessel as tissue is bluntly dissected away from the vessel and around side branches within the cavity, and it is highly desirable to have endoscopic instruments selectively available at the distal end of an elongated device that is manipulable within the insufflated anatomical space through a gas-seal to occlude and sever side branches of the saphenous vein in preparation for harvesting of the vessel from the patient's body. Similarly, it is highly desirable to establish minimally invasive techniques for harvesting a radial artery.

However, harvesting an arterial conduit is more difficult and hazardous than harvesting a venous conduit. Inadvertent transection of an arterial side branch during tissue dissection leads to hemorrhage from the artery, which is under high pressure. The dissection tunnel immediately fills with blood, and prevents visualization of the vessel for further exposure of the artery. If a side branch is stretched and partially avulsed or torn, the high pressure in the artery causes blood to dissect along the medial and adventitial layers of the artery, expanding the wall of the artery like a balloon, and ruining the vessel for use as a graft.

SUMMARY OF THE INVENTION

In accordance with an embodiment of the present invention, an elongated tissue-dissecting endoscope includes a blunt tissue-dissecting tip at the distal end of a rigid shaft for visualizing tissue at the surgical site at which connecting tissue is bluntly dissected away from the vessel. This procedure may be effected through an initial incision through which the vessel is exposed, and in which a sliding gas seal is installed to facilitate insufflation of the anatomical space that is formed about the vessel as connecting tissue is dissected away from the vessel along its course by the tip at the distal end of the tissue-dissecting endoscope.

After sufficient length of the vessel is dissected away from connecting tissue, the dissecting endoscope may be withdrawn from the cavity thus formed, and the tissue-dissecting tip removed therefrom (if installed as a removable tip) to accommodate reconfiguring the dissecting endoscope with an overlying tool cannula. Alternatively, a different endoscope with no dissecting tip can be used in the tool cannula. The tool cannula carries bipolar scissors, bisector, or other transecting or ligating device (e.g., a clip applier, an ultrasonic or radio frequency cauterizer), and a vein retractor or other surgical effector that are each selectively deployable from the open distal end of the tool cannula for selectively manipulating tissue and the vessel such as the saphenous vein as side branches are ligated (e.g., cauterized) and transected along the course of the vessel. The proximal end of the tool cannula includes controls for selectively deploying and manipulating the bipolar scissors or vein retractor or other type of surgical effectors such as operating the bipolar scissors in electrocauterizing and severing modes. Various configurations of proximal-end control devices mounted on the tool cannula facilitate manual manipulation at the distal end of the surgical effector devices during the procedures required to isolate the vessel from side-branch vessels within the bluntly-dissected and insufflated cavity formed in the surrounding tissue. The dissecting endoscope with an overlying or adjacent tool cannula in one of a plurality of configurations of surgical effectors may be inserted through and manipulated within the sliding-gas seal of an access port that is disposed within the initial incision to facilitate convenient side-branch cauterization and transection within the cavity in preparation for harvesting of the vessel from the patient's body.

Harvesting an artery such as the radial artery in accordance with an embodiment of the present invention involves temporary use of a tourniquet proximal to the artery to be harvested in order to cut off flow through the artery during endoscopic harvesting. The extremity containing the artery to be harvested may be externally wrapped prior to activation of the tourniquet. The external wrap exsanguinates the extremity by forcing blood out of the arteries and veins, and the tourniquet maintains the bloodless state in the vessels. In one embodiment of the invention a less significant structure such as a vein adjacent to the artery is tracked using the transparent blunt tip of the dissecting endoscope to form a cavity around the artery without exerting shear force directly on the wall of the artery. Any arterial branches that are avulsed during harvesting are avulsed away from the main trunk of the artery. Many arteries are paired with a vein, and dissection of a cavity around a vein using the dissecting endoscope will also form a cavity around the artery, with much less risk of injury to the artery.

In the case of the radial artery, small diameter veins termed "venae comitantes," lie on each side of the artery, and run along the length of the artery, as shown in FIG. 1A.

BRIEF DESCRIPTION OF THE DRAWINGS

FIG. 1B is a perspective view of a dissecting endoscope according to one embodiment of the present invention;

FIG. 4 is a pictorial illustration of an optically-enhanced tissue-dissecting tip attached to a dissecting endoscope according to the present invention;

FIG. 5 is a perspective view of another attachment structure according to the present invention;

FIGS. 6A and 6B are partial exploded and sectional views of another attachment structure according to the present invention;

FIGS. 13 and 14 are partial perspective views of rotational tissue cutters according to the present invention;

FIG. 17 is a pictorial illustration of another embodiment of a tissue cutter in accordance with the present invention;

FIG. 19 is a pictorial illustration of a tissue cutter combined with a tissue-dissecting tip in accordance with the present invention;

FIGS. 20A and 20B are partial pictorial illustrations of another embodiment of a tissue cutter combined with a tissue-dissecting tip in accordance with the present invention;

FIGS. 21A and 21B are pictorial illustrations of a tissue cauterizing and cutting device according to one embodiment of the present invention;

FIGS. 30A and 30B are perspective views of modified vessel retractors in accordance with other embodiments of the present invention;

FIG. 37 is an exploded perspective view of components assembled in a kit for harvesting a vessel;

FIGS. 38A and 38B comprise a flow chart illustrating a vessel harvesting procedure in accordance with the present invention.

DETAILED DESCRIPTION OF THE INVENTION

Figure 1A:
FIG. 1A is a pictorial illustration of the radial artery and adjacent veins within a forearm.

Vessel Harvesting.

In accordance with the present invention, a vessel such as the saphenous vein in the leg or the radial artery in the forearm is selectively harvested for use in another part of a patient's body, for example, as a graft vessel in coronary arterial bypass surgery. The vessel harvesting proceeds with conventional preparation of the patient's leg or forearm for an initial incision at a selected location along the course of the vessel, such as at the knee, groin or ankle for the saphenous vein, or at the wrist for the radial artery, followed by manual tissue dissection to expose the vessel beyond the initial incision. An anatomical space is formed in tissue surrounding the vessel to an extent sufficient to introduce an access port such as a hollow trocar for gas-tight sealed engagement within the incision.

In accordance with an embodiment of the invention, a rigid endoscope as more fully described later herein is configured at the distal end with one or other surgical effector devices and is introduced through a sliding gas seal within the access port in order to dissect tissue away from the saphenous vein along its course. The anatomical space thus formed along the vessel is simultaneously insufflated with gas under pressure to hold the space open and facilitate convenient dissection of tissue away from the vessel and its associated side-branch vessels, as well as to provide a tamponade effect on the exposed vessels and tissue.

The distal end of the tissue-dissecting endoscope is configured with a rigid tapered tip of transparent material to facilitate visualization through the tip of tissue being dissected by the tip along the course of the vessel. Adherent tissue may be so dissected away from anterior portions of the vessel, followed by dissection of tissue in similar manner away from posterior portions of the vessel in order to isolate the vessel and adjacent portions of side-branch vessels from adherent tissue. Alternatively, tissue may be dissected from posterior portions of some vessels followed by dissection of tissue from anterior portions.

The dissecting endoscope may then be withdrawn from the anatomical space thus formed in dissected tissue along the course of the saphenous vein to be reconfigured in accordance with the present invention with additional instrumentation as later described herein for performing additional surgical procedures associated with harvesting the saphenous vein. Specifically, an elongated sheath or tool cannula carrying surgical effector devices may be disposed about or adjacent the dissection endoscope to selectively position such surgical effector devices as vein retractor, tissue shears, bipolar electrocauterizer, and the like, at selected locations within the anatomical space along the course of the saphenous vein. The dissecting endoscope as reconfigured with associated sheath or tool cannula is introduced through the access port into the anatomical space previously formed along the course of the saphenous vein. Side-branch vessels may be ligated and transected under visualization through the dissecting endoscope in response to manipulation of selected surgical effector devices that are disposed at the distal end of the cannula in response to manual manipulation of controls that are positioned near the proximal end of the cannula. A segment of the saphenous vein thus isolated from adherent tissue and side-branch vessels may then be removed from within the insufflated anatomical space for subsequent preparations and use in another part of the patient's body.

The radial artery, as illustrated in FIG. 1A, may be harvested in accordance with an embodiment of the present invention as follows.

A mark may be made on the skin at the wrist overlying the pulse of the radial artery. A sterile marking pen may be used for this purpose. The lower arm is wrapped with an elastic band (Esmarch bandage) to force blood out of the limb, followed by application of an inflatable tourniquet to the upper arm. The Esmarch bandage is removed, and a skin incision is made in the wrist at the spot marked at the site of the radial artery. Blunt dissection is performed using Metzenbaum scissors to expose the radial artery 4 and the adjacent veins, the venae comitantes 5. The tapered tip 11 of the dissecting endoscope 9, as shown in FIG. 1B, is placed on the anterior aspect of one of the veins 5 lying adjacent to the radial artery with a hollow trocar disposed around the endoscope for forming a sliding gas seal therewith. The tip 11 is advanced sufficiently far to allow the balloon of the trocar to be sealed within the incision to initiate gas insufflation in the arm. The vein 5 is tracked to the antecubital space at the elbow, and the endoscope 9 is then pulled back to the trocar and advanced on the posterior aspects of the vein 5. Next, the tip 11 of the endoscope 9 is placed on the anterior surface of the vein 5 on the other side of the radial artery 4. Anterior dissection and posterior dissection on the second vein 5 is performed. The tip 11 of the endoscope 9 is used to expose both venous and arterial branches along the length of the tunnel, until a pedicle consisting of the radial artery 4 and its adjacent paired veins 5 has been isolated. The endoscope 9 is removed from the tunnel, and a tool cannula, as described in detail later herein, is introduced to cauterize and transect the venous tributaries and arterial branches emanating from the isolated radial artery pedicle. Cauterization and transection of the side branches and tributaries are performed as they appear, with the side branches and tributaries closest to the trocar taken down first. The procedure continues with cauterization and transection, working from the wrist to the elbow, until all connections have been severed. A small counterincision is performed at the elbow, and the pedicle consisting of radial artery and paired veins is ligated with a suture and transected. The pedicle is likewise ligated and transected at the wrist, to complete the harvest of the radial artery pedicle. The tourniquet is deflated, and any bleeding points are identified and cauterized, and the incisions are then closed to complete the procedure.

The procedure described above may be used to harvest other delicate structures in the body. For example, if endoscopic harvest of a nerve is desired, and a vein runs parallel to the nerve, the vein may be tracked with the dissecting endoscope 9 to expose the nerve with less potential for nerve injury. For example, the sural nerve lies close to the lesser saphenous vein in the posterior aspect of the lower leg, and endoscopic harvest of the sural nerve may be accomplished by tracking along the lesser saphenous vein to form the working cavity around the nerve. Harvest of the internal mammary artery may also be performed by tracking along the adjacent internal mammary vein, followed by cauterization and transection of venous and arterial branches. An internal mammary artery pedicle is harvested, similar to the radial artery pedicle, but with one less vein attached.

Dissecting Endoscope.

Referring now to the perspective view of FIG. 1B, there is shown a tissue-dissecting endoscope 9 in accordance with one embodiment of the present invention that is fitted with a blunt tissue-dissecting tip 11 which includes transparent rigid, substantially conically-tapered walls that are aligned within the field of view through the dissecting endoscope 9. The dissecting endoscope 9 is formed within a rigid tube 10 that is substantially filled with optical imaging and illumination components and that is sufficiently rigid to protect the internal optical component from damage while withstanding the forces, torques, and bending moments encountered during tissue dissection along the course of a vessel such as the saphenous vein. The degree of rigidity or stiffness of the rigid tube 10 and internal components is determined with reference to its optical characteristics while under bending forces. Specifically, adequate visualization must be provided via image quality and light intensity during and after exertion of bending forces on the dissecting endoscope 9. Thus, no significant change in the image (i.e., loss of image at an edge of the field of view) should occur during bending or deflection of the endoscope 9 by up to 10% of the length thereof (i.e., about 40 mm deflection over about 405 mm of working length). Similarly, the optical characteristics evaluated after deflection of about 22% of the working length should indicate no permanent optical damage or loss of image at an edge of the field of view. The rigid tube 10 has a diameter of about 7 mm and includes one or more segments 12, 14 of reduced diameter near the distal end to facilitate attachment and sealing thereto of various surgical effector devices and tip attachments. In one embodiment of the present invention, as illustrated in FIG. 1B, the rigid tube 10 of the dissection endoscope 9 includes screw threads 17 disposed near the distal end along a distal segment 12 of reduced diameter to mate with threads carried on a surgical effector device such as the tissue-dissecting tip 11. Additionally, the distal end of the rigid tube 10 may include an intermediate segment 14 of diameter greater than the distal segment 12 and less than the rigid tube 10 to mate in axial alignment with a corresponding bore in a surgical effector device such as tip 11, thereby to facilitate alignment for threaded attachment of the tip 11 to the distal segment 12 of the rigid tube 10.

The tissue-dissecting tip 11 includes rigid, transparent walls that taper internally toward a cusp or apex and externally toward a blunt or rounded tip that facilitates dissecting tissue without puncturing the vessel being harvested or its side-branch vessels. The tip 11 is mounted forward of the distal end of the dissecting endoscope 9 within its field of view to provide visualization with low distortion of tissue being dissected by advancement of the dissecting endoscope 9 and tip 11 through tissue along the course of the vessel to be harvested (e.g., the saphenous vein). Additionally, the tapered walls or center of the tip 11 may carry markings to provide visual cues regarding the orientation and location of the tip 11 and endoscope 9 relative to a vessel being harvested. In addition, translucent or colored (e.g., blue) tips 11 can be used to aid in visualization and differentiation between tissue types and structures.

Figure 2B:
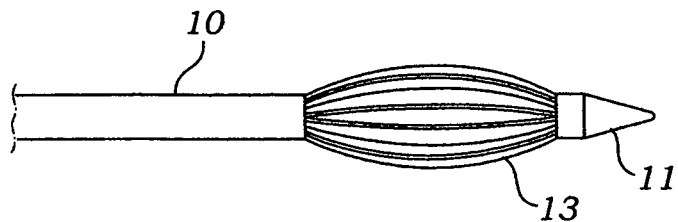
FIGS. 2B and 2C are, respectively, front and end views of another embodiment of a tissue dilator in accordance with the present invention.
Figure 2C:
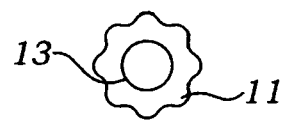
Figure 3A:
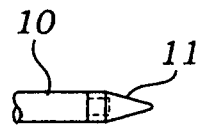
FIGS. 3A-3C are partial side views of tissue-dissecting tips and dilators attached to the distal end of a dissecting endoscope according to the present invention.
Figure 2A:
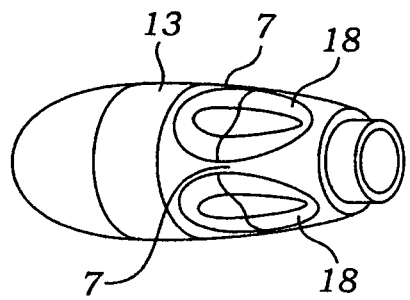
FIG. 2A is a perspective view of a tissue dilator having faceted surfaces according to the present invention.

A tissue-dilating collar 13 may optionally be disposed near the distal end of the dissecting endoscope 9, proximally displaced from the tip 11, to promote expansion of a cavity or anatomical space adjacent a vessel such as the saphenous vein as the dissecting endoscope 9 and attached tip 11 are advanced through surrounding tissue along the course of the vessel to be harvested. The tip 11 and dilator 13 may be formed as an integral assembly for threaded attachment, or other type of attachment as later described herein, to the distal end of the dissecting endoscope 9. The dilator 13 may be shaped similar to an olive to further expand tissue that is initially dissected by the tip 11 as the tip 11 and dilator 13 are advanced through tissue along the course of a vessel. In accordance with an alternative embodiment of the present invention, the tissue dilator 13 may include faceted surfaces 18 disposed about the periphery thereof in the forward portion of the dilator, as shown in FIG. 2A. These faceted surfaces 18 reduce the frontal area of the tip 11 and distal end of the dilator 13 that must penetrate tissue to create a more gradual transition to the maximum sectional dimension of the dilator, and thereby reduce the axial force required to be applied to the dissecting endoscope 9 for dissecting and dilating tissue along the course of a vessel. Additionally, the faceted surfaces 18 form ridges 7 that may be rotated within penetrated tissue to further reduce the longitudinal forces required to dissect and dilate tissue along the course of a vessel. The proximal end of the dissecting endoscope 9 includes fittings 15, 16 for attachment of a conventional medical camera coupler (not shown), and a conventional fiber optic light guide (not shown), and the like. Of course, the tissue dilator 13 may also include a generally axially-aligned ribbed and fluted outer surface, as illustrated in FIGS. 2B and 2C, with the distal edge of the dilator 13 displaced proximally from the tip 11.

Figure 3B:
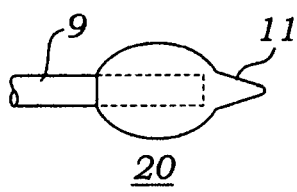
Figure 3E:
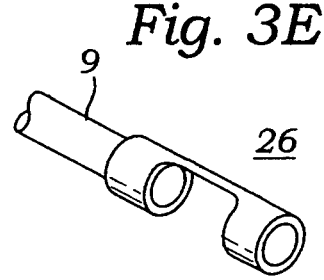
FIGS. 3D-3F are perspective views of surgical effector devices selectably attached to the distal end of a dissecting endoscope according to the present invention.
Figure 3D:
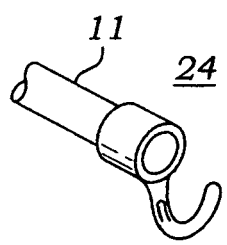
Figure 3C:
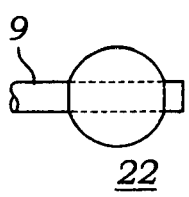
Figure 3F:
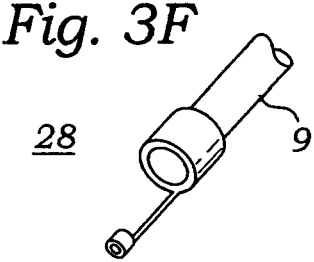

Referring to FIGS. 3A-F, there are shown side and perspective views of additional other surgical effector devices 19, 20, 22, 24, 26 and 28 that may be conveniently attached to the distal end of the dissecting endoscope 9 in mating engagement with the threads 17 carried by the distal segment 12 of the endoscope 9. Specifically, various sizes and configurations of tissue dilators 19, 20, 22, with or without a tapered tissue-dissecting tip 11, may be secured to the distal end of the dissecting endoscope 9 via threaded engagement. Additionally, a hook-like extension, as illustrated in FIG. 3D, may be attached via mating threads to the dissecting endoscope 9 to facilitate tracking along a saphenous vein around its intersections with side-branch vessels, and the like, within the field of view from the end of the dissecting endoscope 9. Similarly, an extension carrying a 'C'-shaped forward edge, as illustrated in FIG. 3E, may be attached via mating threads to the distal end of the dissecting endoscope 9 in order to pass along the course of the vessel and thereby facilitate cleaning off of remaining adherent tissue within the field of view from the distal end of the dissecting endoscope 9. Also, a suture-positioning or knot-pushing extension, as illustrated in FIG. 3F, may be attached via mating threads to the distal end of the dissecting endoscope 9 to facilitate ligating the vessel or side-branch vessels within the field of view from the distal end of the dissecting endoscope 9. And, tissue-dissecting tips of various optical characteristics, for example, as illustrated in FIG. 4, may also be attached via mating threads 17 to the distal end of the dissecting endoscope 9 in optical alignment therewith. Specifically, the tissue-dissecting tip 29 may be formed as a solid transparent component with forward tapered conical walls tapering toward a blunt tissue-dissecting tip 31 from an intermediate region of greater diameter that is aligned along tapering walls 30 which diverge at substantially the angle of the field of view from the distal end of the dissecting endoscope 9. Mating optical faces may include a concave recess 32 intermediate the tip 29 and viewing end of the dissecting endoscope 9 to produce a specific magnification (e.g., telescoping or wide-angle) or non-magnification within the field of view of the endoscope 9.

It should be noted that other attachment structures may be formed near the distal end of the dissecting endoscope 9 to engage with various surgical effector devices. Specifically, as illustrated in FIG. 5, one or more lateral protrusions 40 may be disposed near the distal end of the dissection endoscope 9 for longitudinal sliding fit along one or more corresponding slots 21 in the internal bore 23 through the dilator 13, to resilient abutment of an O-ring seal 25 against a proximal shoulder 27 within the bore 23. Further insertion of the dissection endoscope 9 and protrusion 40 into the bore 23 facilitates rotational orientation of the protrusion 40 along the distal shoulder 20, into resilient engagement within detent 6 in the distal shoulder 20. The tip 11 and dilator 13 are thus quickly detachable from the distal end of endoscope 9 and are sealed onto the endoscope 9 by O-ring 25 compressed within bore 23 and abutting proximal shoulder 27. Alternatively, various surgical effector devices may be attached to the distal end of the dissecting endoscope 9 via various press-lock or snap-fit attachment structures as illustrated in FIGS. 6A and 6B. Specifically, one embodiment of an attachment structure includes a resilient ring 35 near the distal end 36 of the dissecting endoscope 9 for mating with a ringed recess 37 within the sliding bore 38 in the surgical effector device 40 (e.g. a dissecting tip and dilator combination). In this embodiment, a solid, elastic dilator 39 may include an inwardly extending lip 41 near a proximal end of the dilator to form an elastic, fluid-tight seal against the outer perimeter of the segment of the dissecting endoscope 9 with which the lip engages. A similar attachment structure may be formed within the tissue-dissecting tip directly in the absence of a tissue dilator attached to the proximal end of such tip.

Figure 6C:
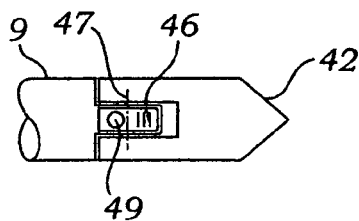
FIG. 6C is a partial pictorial illustration of another locking structure according to the present invention.

In another embodiment, the attachment structure includes a lever-actuated locking device, as illustrated in FIG. 6C. Specifically, the tissue-dissecting tip 42 (or a tissue dilator formed about the proximal end of such tip) carries one or more levers 46 that are axially aligned and are rotatable about a lateral pivot axis 47 to actuate a locking pin 49 mounted on the lever 46 on the proximal side of the pivot axis 47. In this attachment structure, pressing the lever 46 on the distal side of the pivot axis 47 elevates the locking pin 49 from its mating recess in the dissection endoscope 9. Alternatively, the locking pin 49 may be affixed to the dissection endoscope 9, and a mating recess may be carried on the lever for similar press-to-unlock attachment of a surgical effector device such as a tissue-dissecting tip to the distal end of the dissection endoscope 9.

Figure 7B:
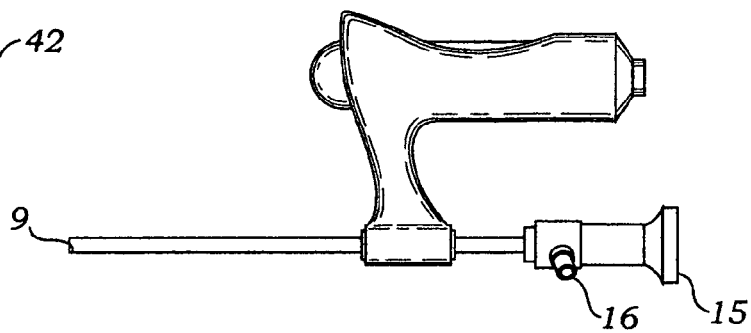
FIGS. 7A and 7B are pictorial illustrations of in-line and offset handles, respectively, attached to the proximal end of a dissecting endoscope in accordance with the present invention.
Figure 7A:
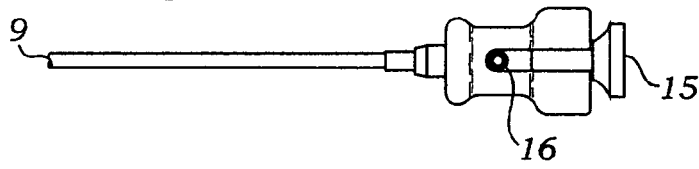

The dissection endoscope 9 thus initially configured with a tissue-dissecting tip attached to the distal end may be used to dissect tissue away from a vessel such as the saphenous vein as the surgeon grasps the rigid body of the dissecting endoscope 9 near the proximal end thereof in order to manipulate the tip 11 through the tissue along the course of the vessel. To facilitate grasping and manipulating the dissecting endoscope 9, various styles of handles, as illustrated in FIGS. 7A and 7B, may be attached near the proximal end of the dissecting endoscope 9. In-line styles of handle such as illustrated in FIG. 7A and offset styles of handle such as illustrated in FIG. 7B promote the surgeon's comfort and control during use of the dissecting endoscope 9 in the procedure as previously described to isolate a vessel such as the saphenous vein for harvest from a patient's body.

Vessel Harvester.

Figure 8:
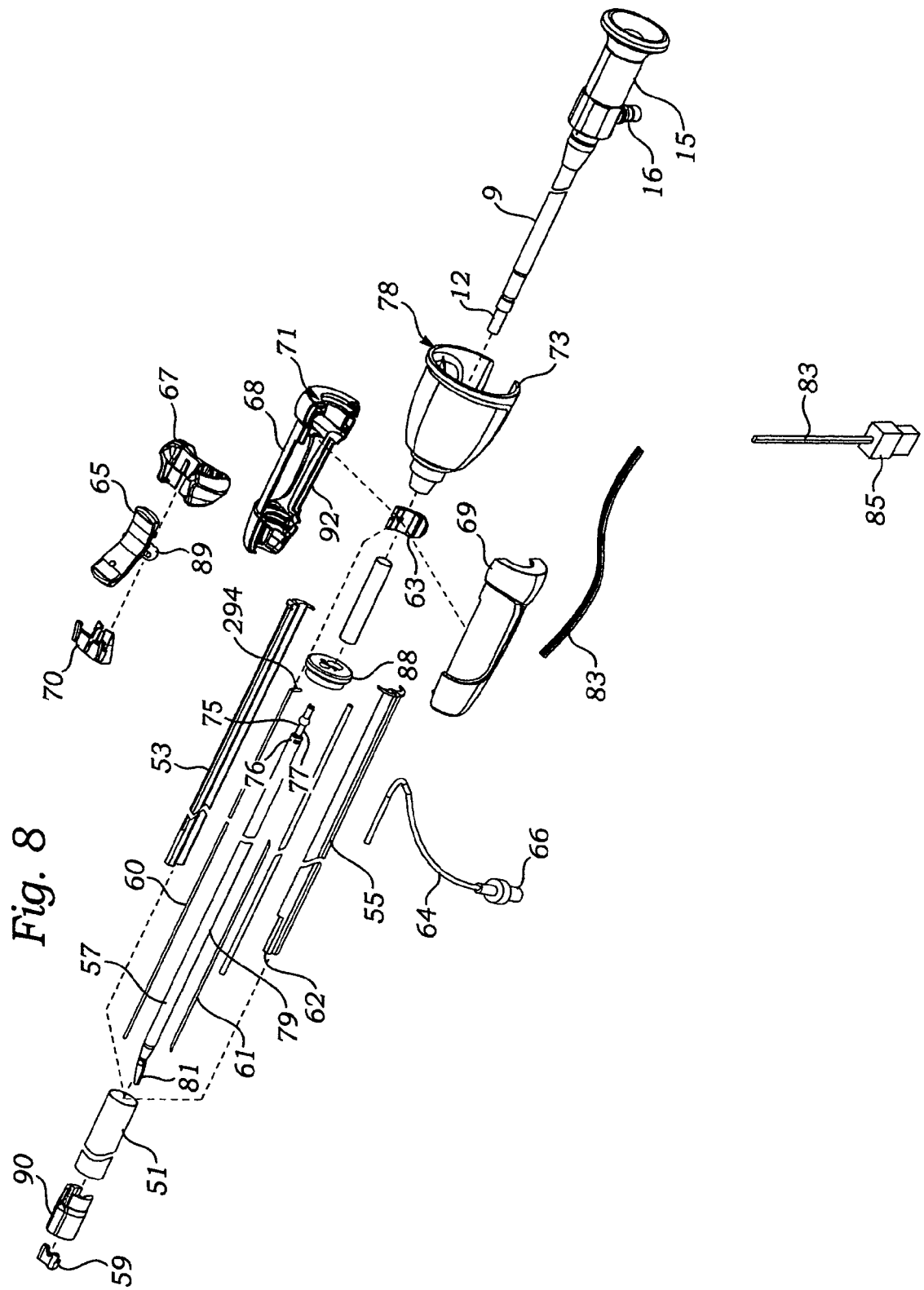
FIG. 8 is an exploded view of a vessel harvester in accordance with one embodiment of the present invention.

Referring now to FIG. 8, there is shown an exploded view of a dissection endoscope 9 and an overlying sheath or tool cannula 51 that supports various surgical effector devices, as later described herein, and that receives the endoscope 9 axially within a lumen which extends between proximal and distal ends of the cannula 51. The tool cannula 51 may be modified for orientation along side the endoscope 9 in a manner similar to configurations as later described herein, for example, with reference to FIGS. 10-12. The tool cannula 51 has sufficient length to extend from a patient's knee to groin, or knee to ankle, or wrist to elbow. The dissection endoscope 9 (or other endoscope) thus configured may be used in the surgical procedures that are involved following dissection of tissue away from a vessel in order to harvest the vessel from the patient's body. Specifically, the tool cannula 51 houses a pair of elongated mating half shells 53, 55 that form separate lumens for an elongated scissor assembly 57 and a vein retractor 59, 60 and irrigation conduit 61. These devices are manually controllable at the distal end of the tool cannula 51 in response to control members 63, 65, 67 that are supported within the mating housing shells 69, 71, and that are linked to the surgical effector devices through the lumens of tool cannula 51. The tool cannula 51 and attached housing 69, 71 rotate about a bell-shaped segment of the housing 73 that is retained in alignment with the dissection endoscope 9 by snap-fit attachment to the light port 16 thereon. This structure thus supports requisite surgical effector devices, as later described herein in detail, for performing surgical procedures within an anatomical space that was previously dissected in tissue adjacent the saphenous vein of a patient, in the manner as previously described. Specifically, the elongated scissors 57 include a pair of rods 75, 77 disposed within a sheath 79. A pair of scissor blades 81 are pivotally mounted on an axle that is supported on the sheath 79, and the blades 81 are actuated through conventional linkage by the relative sliding movement of the rods 75, 77 within sheath 79. Rods 75, 77 may also serve as electrical conductors for applying bipolar cauterizing signals to the individual scissor blades 81, or to electrodes supported thereon. Electrical connections are made to the rods 75, 77 within the housing 69, 71 via cable 83 and the connector 85 that extends from the housing. The scissor blades 81 may be selectively extended and retracted relative to the distal end of the tool cannula 51 by sliding the control member 67 axially along the housing 69, 71 in engagement with the sheath 79. The control member 67 pivotally supports the lever 65 thereon that links to the rods 75, 77 in such manner that rocking the lever 65 pivoted on the control member 67 advances and retracts the rods 75, 77 relative to the sheath 79 to operate the scissor blades 81 through shearing movement about their common pivot.

A vessel retractor 59 is also supported in the tool cannula 51 on sliding wire support 60, as shown in FIG. 8, for selective deployment and retraction relative to the distal end of the tool cannula 51 in response to axial sliding movement along the housing 69, 71 of the control member 63 that is linked thereto. The generally 'C'-shaped vessel retractor 59 is supported near one side edge by the wire 60 and is supported near the other side edge by the tube 61 that slides within tube 62. In this way, a sliding fluid connection is provided to a nozzle in the vessel retractor 59 for washing the distal lens of the dissecting endoscope 9. The proximal end of the tube 62 is attached within the housing 69, 71 to the flexible supply tubing 64 that extends from the housing 69, 71 to a fluid connector 66. A resilient seal 88 is disposed within the tool cannula 51 about the support wire 60 and scissor sheath 79 and supply tube 62 and an installed dissecting endoscope 9 to maintain a gas-tight sliding seal during operation of the structure within an insufflated surgical environment. The control member 67 that is slidably mounted on the housing 69, 71 may retain the scissor sheath 79 in fixed angular orientation relative to the tool cannula 51 via linkage to flat surfaces 76 near the proximal end of the scissor sheath 79. Alternatively, the scissor sheath 79 may rotate axially relative to the cannula 51 via linkage to an annulus or peripheral groove attached to the sheath 79 near the proximal end thereof. Also, the distal end segment 12 of the endoscope 9 may be reduced in diameter and support an attachment structure thereon, as previously described, and such segment of reduced diameter, with no attachments thereon, also facilitates nesting surgical effector devices within the distal end of the tool cannula 51. Such distal end 90 may include a chamfered or rounded forward edge to minimize snagging on tissue and to promote maneuverability of the tool cannula 51 within a cavity of dissected tissue along the course of a saphenous vein or radial artery.

Figure 9:
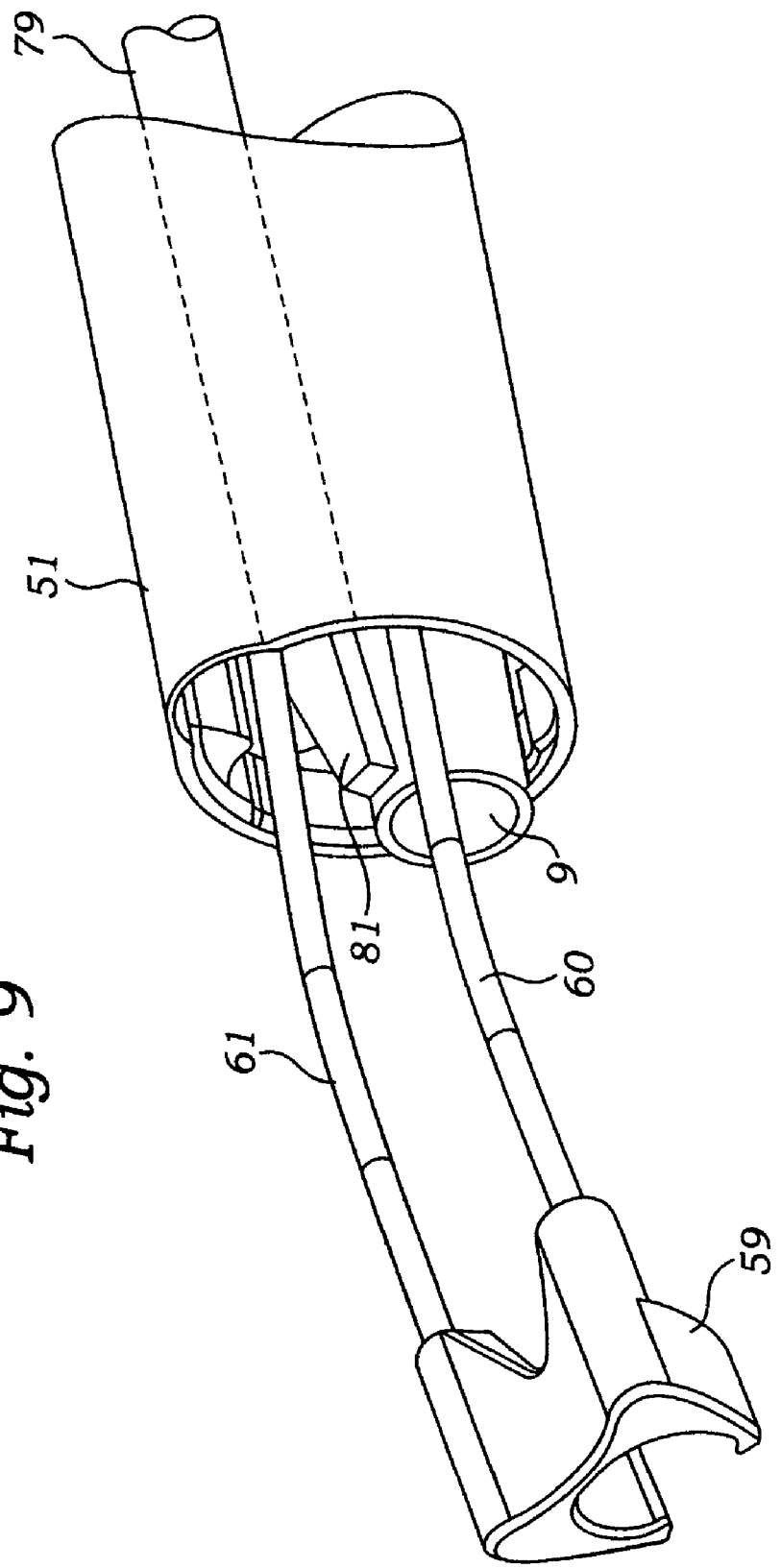
FIG. 9 is a perspective view of the distal end of one embodiment of a vessel harvester according to the present invention.

Referring now to the perspective view of FIG. 9, the viewing end of the endoscope 9 (without tip 11) is disposed within the open distal end of the tool cannula 51, surrounded by, for example, supports 60, 61 for a vein retractor 59, and the shaft 79 attached to bipolar scissors 81, as a representative set of surgical effector devices that are deployable and manipulatable relative to the distal end of the tool cannula 51. Other types of effector devices carried by the tool cannula 51 for deployment and manipulation relative to the distal end thereof may include, for example, one or more of an endoscope washing nozzle, a knot pusher for positioning a suture about the vessel being harvested, a clip applier for occluding lateral or side-branch vessels, an irrigating or suction port, a ligator, hot-element cauterizer, and a fork device, as later described herein, for surrounding, cauterizing, ligating or transecting side-branch vessels.

The vessel retractor 59, as a surgical effector device as shown in the illustrated embodiment of FIG. 9, is configured generally as a C-shaped device to slide along a saphenous vein or a vein adjacent a radial artery being harvested, and is mounted on resilient support 60, 61 for independent deployment from the open distal end of tool cannula 51 in response to axial movement of the control member 63 slidably mounted in the housing 69, 71 at the proximal end of the cannula 51. The resilient supports 60, 61 of the vessel retractor 59 facilitate selective lateral displacement of a saphenous vein or radial artery pedicle in response to manual manipulation of the control member 63 in a manner similar to the vein retractor that is more fully described, for example, in U.S. Pat. No. 6,162,173.

The bipolar scissors 81, as another surgical effector device, shown in FIG. 9 are supported on the distal end of sheath 79 for independent deployment from the open distal end of tool cannula 51 in response to manual sliding movement of a control member 67 shown in FIG. 8 that is slidably mounted in the housing 69, 71 at the proximal end of the tool cannula 51. In addition, the lever 65 shown in FIG. 8 that is pivotally supported on the control member 67 may be manually manipulated about its pivot to selectively open and close the scissor blades 81 via the linkage 75-77, as previously described. Alternatively, both the scissors 81 and the retractor 59 may be slidably deployed together from the open distal end of the tool cannula 51 in a configuration which includes linking of the scissor blades 81 to the retractor 59 or to the supports 60, 61 therefor. In such configuration, a selected distance or spatial separation is maintained between a saphenous vein or radial artery pedicle being harvested and the location relative to a junction of a side branch with the saphenous vein or radial artery at which the side branch may be cauterized and transected by the bipolar scissors 81.

It should be noted that the surgical effector devices including vessel retractor 59 and bipolar scissors 81, or other surgical effector devices for electrocauterization and transection of tissue and vessel structures, are mounted within the tool cannula 51 which may be fully rotatable about the endoscope 9. This provides complete orbital orientation about the elongated axis of the endoscope 9 that remains at substantially fixed rotational orientation for maximum versatility in retracting, ligating or cauterizing and severing tissue and vessel structures within the viewing field forward of the endoscope 9. Viewed images thus remain stably oriented for the user as the tool cannula 51 and the surgical effector devices mounted therein are axially rotated about the endoscope 9 during vessel harvesting procedures. A pointer device or optical marker may be disposed within the viewing field of the endoscope 9 to provide visual orientation of the tool cannula 51 relative to the axis of the endoscope 9 and to facilitate identification of which surgical effector device is deployable and from what location relative to the images viewed through the endoscope 9.

Figure 10:
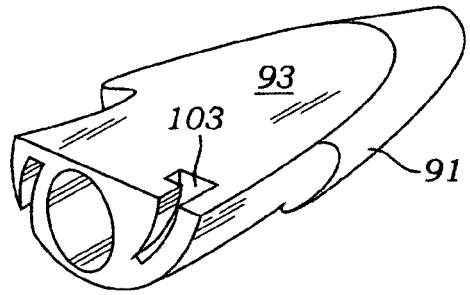
FIGS. 10, 11 and 12 are perspective views of alternative embodiment of vessel harvesters according to the present invention.
Figure 11:
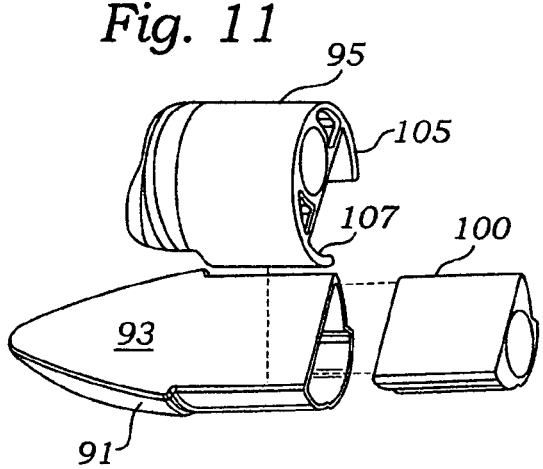
Figure 12:
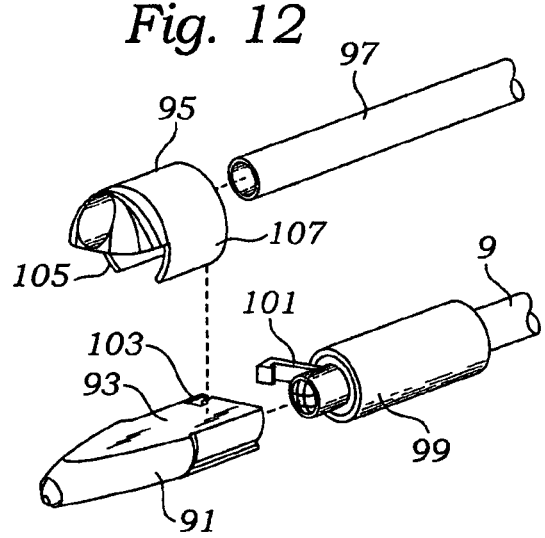

Referring now to the partial perspective views of FIGS. 10, 11 and 12, there are shown perspective views of alternative embodiments of the vessel harvester according to the present invention. Specifically, a dissecting endoscope 9 includes a tapered tissue-dissecting tip 91 that is axially truncated to form a mating surface 93 for selective attachment thereto of a tool housing 95 and associated cannula 97 in eccentric orientation relative to the elongated axis of the dissecting endoscope 9. In this embodiment, the dissecting endoscope 9 includes an attachment structure of its distal end that includes a locking ferrule 99 for quick mating engagement and disengagement with the tissue-dissecting tip 91. In one embodiment, such attachment structure includes a lateral locking arm 101 which mates with a recess 103, as shown in FIG. 10, to inhibit axial and rotational movement of the tip 91 thus attached at the end of the dissecting endoscope 9. Of course, other attachment structures, for example, as previously described or as including insert 100 may be used to selectively attach the tissue-dissecting tip 91 to the distal end of the dissecting endoscope 9.

The mating surface 93 on the tip 91 mates with a similar surface on tool housing 95 which includes descending side walls 105, 107 that are disposed to grip the sides of the tip 91 for firm seating and retention of the attachment to the tip 91. In this configuration, surgical effector devices, for example, of the types described herein, may be mounted in the tool housing and attached cannula 97 for selective deployment and manipulation relative to the distal end of the assembly using control members (not shown) mounted near the proximal end of the cannula 97 via linkage and operation similar to those previously described herein. Such vessel harvesting structure may thus be selectively configured initially for use of the dissecting endoscope alone in dissecting tissue to create an anatomical space along the course of a vessel, with only the tip 91 attached to the dissecting endoscope 9. Thereafter, the tool housing 95 and cannula 97 with associated surgical effector devices mounted therein may be eccentrically attached to the dissecting endoscope 9 to facilitate further surgical procedures within the anatomical space previously dissected in tissue and incident to harvesting the vessel from a patient's body.

Surgical Effector Devices.

Referring now to the partial perspective views of FIGS. 13 and 14, there are shown views of a rotary cauterizing and shearing device according to one embodiment of the invention that is deployable from the distal end of the tool cannula 51. Specifically, one cylindrical segment 45 having an axially-aligned edge 48 may be extended from the distal end of the tool cannula 51, or alternatively may constitute a portion of such distal end. Additionally, another cylindrical segment 50 having an edge 52 that is axially aligned or is skewed slightly is rotatable within the tool cannula 51 and within the segment 45 to provide rotational shearing action along the mating edges 48, 52, as shown in FIG. 14. The edges 48, 52 may also include adjacent electrodes (not shown) for supplying electrical or thermal energy to tissue such as side-branch vessels for cauterizing and occluding the vessels prior to shearing the tissue by rotationally overlaying the segments 45, 50 as shown in FIG. 14. Of course, the deployment and manipulation of the segments 45, 50 to confine and cauterize and ligate tissue within the edges 48, 52 may be controlled from the proximal end of the tool cannula 51 via using conventional linkage coupled therebetween.

Figure 15A:
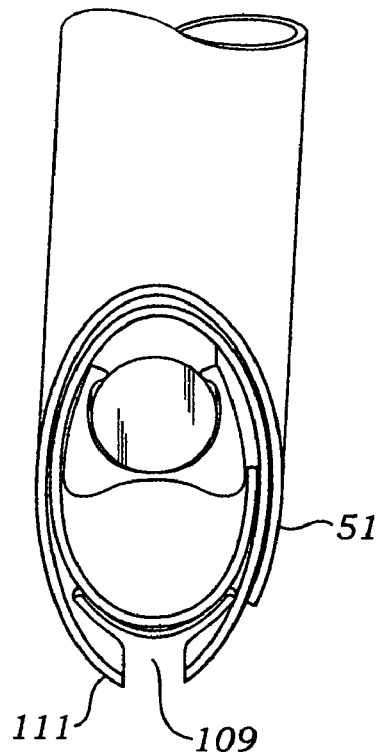
FIGS. 15A and 15B are partial perspective views of alternative embodiments of rotational tissue cutters according to the present invention.
Figure 15B:
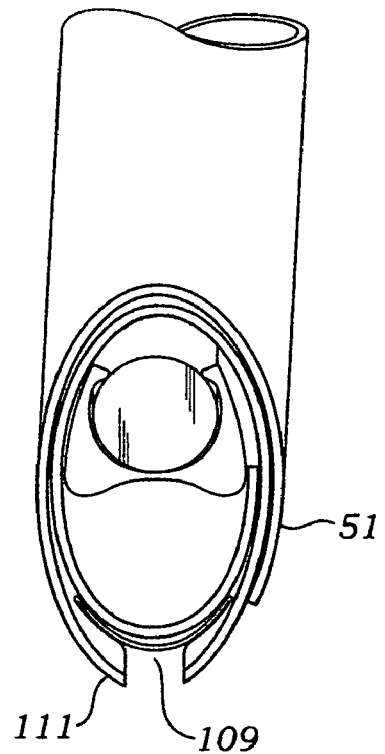

Alternatively, as illustrated in the partial perspective views of FIGS. 15A and 15B, tissue-shearing and electrocauterizing of tissue is greatly facilitated by configuring the distal end of the cannula 51 with a generally 'Y'-shaped or 'T'-shaped slot 109, as shown. In this configuration, an intact side-branch vessel may be manipulated into and then captivated within the slot for convenient shearing in response to lateral extension or rotation of the mating inner segment 111 over the slot 109. Additionally, such shearing mechanism may be energized with electro-cauterizing signal of one polarity, for example, on the cannula 51 and slot 109 and of opposite polarity on the inner mating segment 111.

Figure 16:
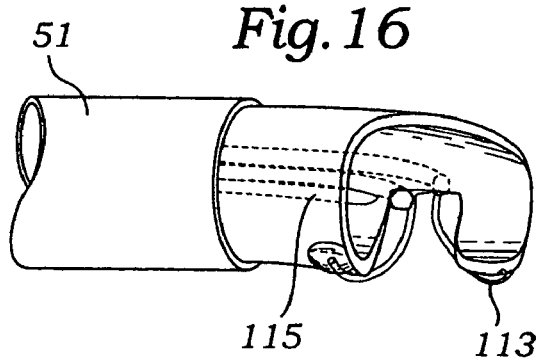
FIG. 16 is a perspective view of another embodiment of a tissue cutter in accordance with the present invention.

In another embodiment of a tissue shearing structure according to the present invention, a hook-like extension 113 may be formed on the distal end of tool cannula 51, as shown in FIG. 16. In this configuration (analogous to a single lateral segment of the slot 111 in the illustrated embodiment of FIG. 15A) a side-branch vessel may be captivated by the hook, and sheared or transected adjacent the hook in response to axial or rotational movement of blade 115 in close proximity to the hook 113.

Alternatively, cauterization and transection of side-branch vessels may be performed using a structure as illustrated in FIG. 17. In this embodiment, a blade 117 that is slidably mounted in the tool cannula 51 is drawn in against an anvil formed by the distal end 90 of the tool cannula 51 to shear tissue or transect a vessel 119 between the blade and anvil. Additionally, electrodes 121, 123 may be disposed on opposite sides of the blade 117 to establish bipolar electrocauterization of a vessel 119 that is positioned against the blade 117 for cutting, and that is therefore also positioned in contact with the electrodes 121, 123.

Figure 18:
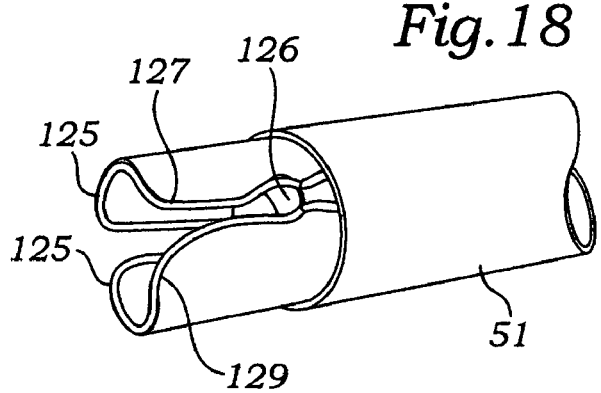
FIG. 18 is a pictorial illustration of another embodiment of a tissue cutter in accordance with the present invention.

Referring now to FIG. 18, there is shown another embodiment of a tissue-cutting device formed at the distal end of the tool cannula 51. In this embodiment, a diametric slot 125 is formed in the distal end of the tool cannula 51 for receiving a side-branch vessel therein that is to be transected (and optionally cauterized). A cutter blade 126 retracts within the tool cannula 51 past the depth of the slot 125 to accommodate positioning of a side-branch vessel completely within the slot 125. Various keyhole or lateral extensions of the innermost segment of the slot 125 may be provided to aid in retaining the side-branch vessel in position for electrocauterization and/or transection. Bare electrodes 127, 129 may be disposed on opposite sides of the slot 125 (on one diametric side of the cannula 51) to provide requisite spacing from the intersection of the vessel with a side-branch vessel to the location thereon at which cauterization and transection are to be performed. The electrodes 127, 129 may be disposed at different diameters of the tool cannula 51 to overlap over the slot 125 without touching in order to assure electrical contacts with the side-branch vessel for effective electrocauterization, and to assist in captivating the vessel within the slot 125 during transection. In these embodiments, the cutter blade 126 may be mounted within the tool cannula 51 to rotate or translate across the slot 125 for transecting a side-branch vessel disposed within the slot 125.

Alternatively, as illustrated in FIG. 19, a tissue-shearing structure may be incorporated with another surgical effector device such as a tissue-dissecting tip. In this illustrated embodiment, a slot 130 is formed in one wall of the tissue-dissecting tip 131 to permit a hook-shaped cutter blade 133 to extend axially through the slot 130 in preparation for captivating within the hook-shaped blade 133 a side-branch vessel to be transected. Additionally, bipolar electrodes 135, 137 may be disposed close to the slot 130 on opposite sides thereof for contacting a vessel to be transected while captivated by the hook-shaped blade 133.

Referring now to FIGS. 20A and 20B, there are shown pictorial illustrations of mating half sections of forceps jaws 141, 143 that are slidably mounted within tool cannula 51 and that, closed, form a tissue-dissecting tip 145 which is suitably shaped for performing blunt tissue dissection. The forceps jaws 141, 143 may be configured as bipolar electrodes, as shown in FIG. 20B, for clasping and electro-cauterizing a side-branch vessel. A cutting blade 147 may be mounted for selective positioning within the jaws 141, 143 (e.g., as by axial movement from within tool cannula 51) in order to facilitate transecting a cauterized vessel upon closure of the jaws 141, 143 about the vessel.

Referring now to FIGS. 21A and 21B, there are shown pictorial illustrations of another embodiment of a tissue cauterizing and shearing structure according to the present invention. Specifically, a relatively inflexible coil 151 is disposed about a central conductor 153 that is spaced away from the inner surfaces of the coil 151 to receive electrocauterizing bipolar signals selectively supplied to the coil 151 and conductor 153. As shown in FIG. 21B, a side-branch vessel 155 is captivated between adjacent convolutes of the coil 151 to contact both the coil 151 and conductor 153 during electrocauterization of the side-branch vessel 155. For this reason, the pitch of the coil 151 is selected to leave spacings between adjacent convolutes of approximately the dimensions of side-branch vessels 155 likely to be encountered during harvesting of a saphenous vein. Alternatively, the pitch of the coil 151 may vary over the exposed length thereof to provide a range of spacings between adjacent convolutes that can accommodate the variations in the dimensions of side branch vessels 155 that are encountered during such harvesting procedures. The coil 151 and center conductor 153 are substantially coaxially positioned by insulator 157 at the distal end of the coil and at a proximal end (not shown) within the supporting sheath 159. Tissue-shearing action is achieved by relatively axially sliding the overlying sheath 159 along the length of the coil 151 to sever a side-branch vessel that is captivated between adjacent convolutes of the coil 151 via a sharpened leading edge of the sheath 159. Alternatively, the coil 151 may overlay the sheath 159 that is disposed within the coil 151 in close proximity of the inner dimensions of the coil 151 and overlaying the central conductor 153. In this configuration, side-branch vessels that are captivated between adjacent convolutes of the coil 151 are severed via a sharpened leading edge of the inner sheath 159 as it is moved axially through the coil 151.

In another embodiment of this electrocauterizing and tissue-shearing structure, a resilient coil 151 and central conductor 153 are mounted for relative movement in order to facilitate collapsing the coil 151 axially and thereby diminishing the pitch substantially to zero. Thus, side-branch vessels that are captivated within the space between adjacent convolutes of the coil 151 while maximally extended are then severed as the convolutes of the coil are compressed. Substantially flat-wound convolutes of coil 151 with sharpened adjacent lateral edges greatly facilitate severing a side-branch vessel captivated between adjacent convolutes. Such electrocauterizing and tissue-shearing structures may be substituted for bipolar scissors of the types previously described herein for use similarly in combination with a vessel retractor, or as otherwise manipulated from the distal end of the vessel harvester.

Figure 22:
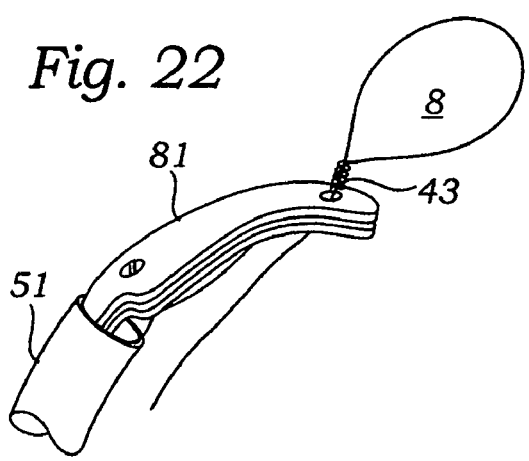
FIG. 22 is a partial perspective view of a surgical effector device for positioning a suture in accordance with the present invention.

Referring now to the partial perspective view of FIG. 22, there is shown another surgical effector device that may be selectively deployed and manipulated from the distal end of cannula 51 under manual control from the proximal end of the cannula 51. Specifically, scissor blades 81 may include an aperture 43 through, or a closed channel along (not shown), one or more of the blades 81 for selectively positioning a suture loop 8 about a vessel to be occluded and severed for harvesting from the body.

Figure 23A:
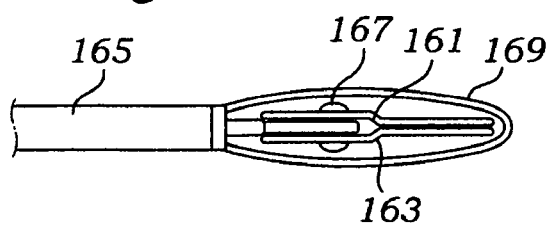
FIGS. 23A, 23B and 23C are partial side views of a tissue cauterizing and cutting device in accordance with the present invention.
Figure 23B:
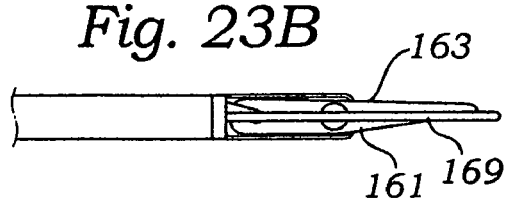
Figure 23C:
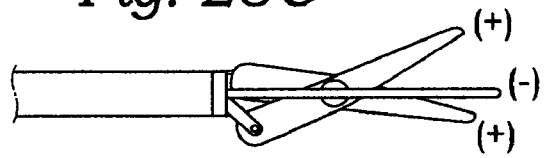
Figure 25A:
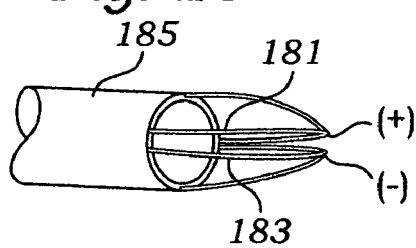
FIGS. 25A-25D are partial perspective views of surgical effector devices in accordance with additional embodiments of the present invention.
Figure 25C:
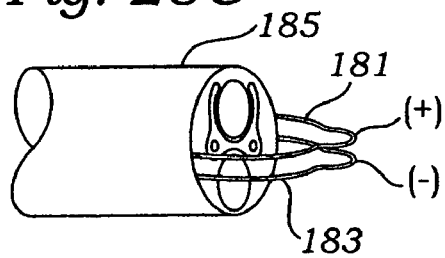
Figure 25B:
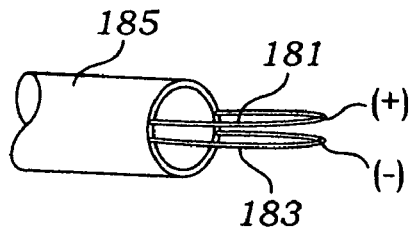
Figure 25D:
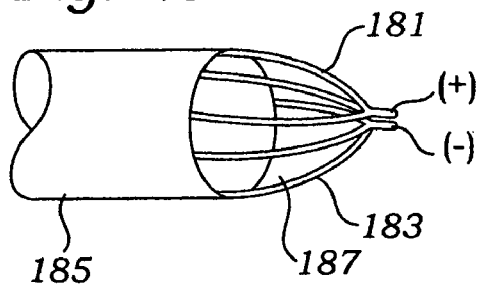

Referring now to FIGS. 23A, 23B and 23C, there are shown partial top and side views of another surgical effector device for electrocauterizing and shearing tissue during a vein-harvesting procedure. In this embodiment, a pair of scissor blades 161, 163 are pivotally mounted on a supporting body 165 for rotation about a pivot 167. In addition, the body 165 also supports a bale 169 spaced about the periphery of the blades 161, 163 and lying substantially in the plane of the pivot 167. In this embodiment, the blades 161, 163 are operable in conventional manner from a proximal location via linkage that couples the blades 161, 163 to a manual control member at the proximal location, in a manner as previously described herein. In addition, the blades 161, 163 may serve in common as an electrode for one polarity of electrocauterizing signal, and the peripheral bale 169 may serve as an electrode for the opposite polarity of electrocauterizing signal. In this configuration, the blades 161, 163 together in closed configuration and the peripheral bale 169 may function as spaced bipolar electrodes for contacting and electrocauterizing tissue. Alternatively, the blades 161, 163 in open configuration and the peripheral bale 169 may captivate a side-branch vessel therebetween for electrocauterization and transecting thereof in efficient manner, particularly if the supporting body 165 is mounted to constrain angular orientation of the blades 161, 163 relative to orientation of a side-branch vessel to be cauterized and transected.

Figure 24A:
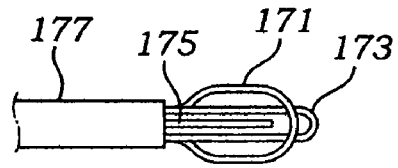
FIGS. 24A-24I are partial top, side, end and perspective views of a tissue cutting and cauterizing devices according to other embodiments of the present invention.
Figure 24B:
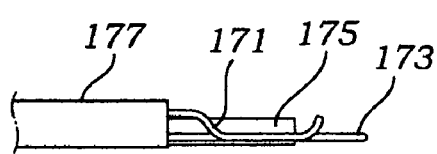
Figure 24C:
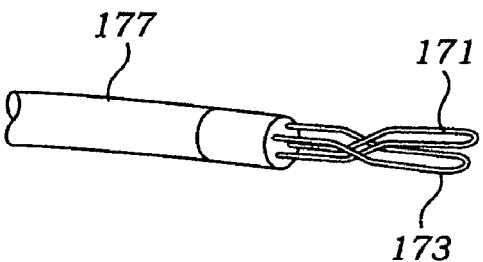
Figure 24D:
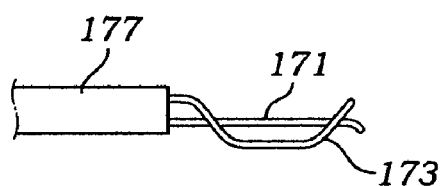
Figure 24E:
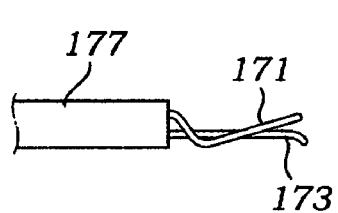
Figure 24F:
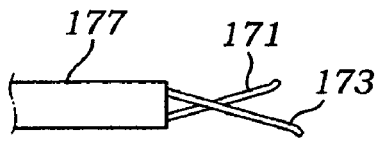
Figure 24G:
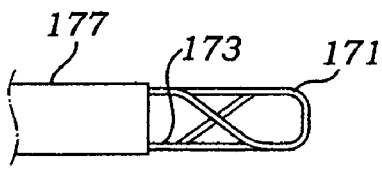
Figures 24H, 24I:
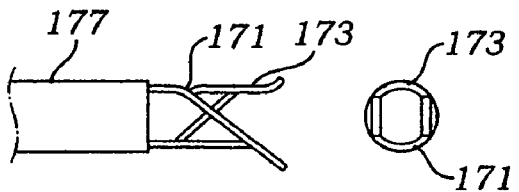

Referring now to FIGS. 24A and 24B, there are shown partial top and side views of another cauterizing and transecting structure in accordance with the present invention. In this structure a pair of resilient wire electrodes 171, 173 are disposed to lay in substantially a common plane over portions of their respective lengths and areas and are spaced away from each other to serve as bipolar electrodes. Alternatively, the electrodes can lie in parallel or skewed planes, or can twist and transition between reference and orthogonal orientations, as illustrated in FIGS. 24C-24I. Accordingly, side-branch vessels captivated between the electrodes 171, 173 resulting from resilient deflection of the electrodes out of the common plane may be electrocauterized by application of signals thereto of opposite polarities. Additionally, a blade 175 with a forward cutting edge or tapered side edge or hooked rearward-facing edge is mounted within body 177 for axial sliding movement within the boundaries of the electrodes to transect a side-branch vessel captivated between the resilient electrodes 171, 173. This structure is typically mounted for convenient axial rotation relative to the course of a side-branch vessel in order to align the structure with a side-branch vessel disposed within the substantially common plane of the electrodes.

Referring now to FIGS. 25A, 25B, 25C and 25D, there are shown partial perspective views of alternative structures for cauterizing tissue. In these embodiments, wire structures 181, 183 are disposed in spaced-apart, substantially plane-parallel orientation at the distal end of supporting body 185. Additionally, these electrodes 181, 183 may be disposed within or on, or form a portion of, a clear plastic conical section or wire cage 187 configured as a tapered tip for bluntly dissecting tissue. In each configuration, the spaced electrodes 181, 183 are connected to receive electrocauterizing signals of opposite polarities, and may be sufficiently resilient to compress through and thereby sever cauterized tissue in side-branch vessels captivated between the electrodes 181, 183.

Figure 26A:
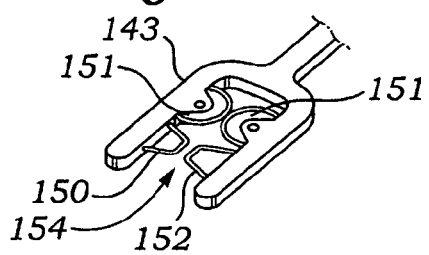
FIGS. 26A and 26B are partial perspective views of surgical effector devices in accordance with additional embodiments of the present invention.
Figure 26B:
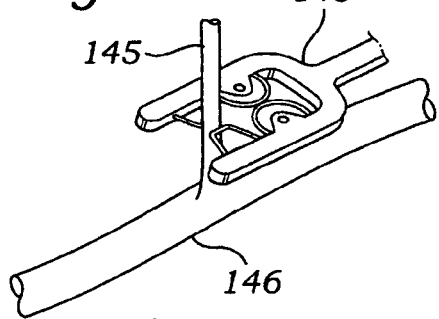

Referring now to the partial perspective views of FIGS. 26A and 26B, there is shown a surgical effector device including a fork-like device 143 having spaced, forward-projecting tines that are disposed to surround side-branch vessel 145 of a vessel 146 being harvested. Each tine includes an electrode 150 that intrudes from the forward end toward the other electrode 152 to form a slot 154 therebetween to admit a side-branch vessel 145 therethrough into the recess between tines. Thus, a side-branch vessel 145 positioned in the slot 154 between electrodes 150, 152 may be electrically or thermally cauterized and occluded by electrical or thermal energy supplied to the electrodes, as shown in FIG. 26B, prior to being transected by cutter blades 151 positioned within the recess of the fork 143 behind the slot 154 between electrodes 150, 152. Of course, other configurations of cutter blade or blades 151 than rotary or circular blades as shown may be arranged behind the slot 154 between electrodes to sever a vessel as the fork-like device 143 is advanced along the course of the vessel being harvested 146 through and past a side-branch vessel 145. For example, angled fixed cutting edge or edges and movable hook-like or lateral cutting blades may also be disposed within the fork-like device 143 behind the electrodes 150, 152 for ligating cauterized side-branch vessels.

Figure 27A:
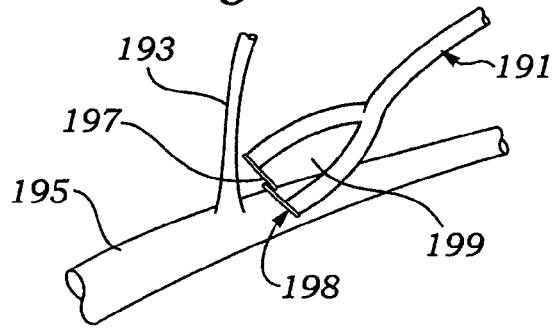
FIGS. 27A and 27B are partial perspective views of a vessel retractor in accordance with one embodiment of the present invention.
Figure 27B:
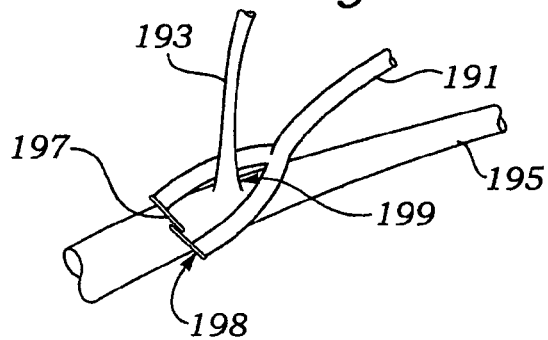

In another embodiment, as illustrated in the partial perspective views of FIGS. 27A and 27B, a fork-like device 191 serves as a retractor for captivating a side-branch vessel 193 as the vessel 195 is deflected or depressed. Specifically, the forward ends of the fork-like device 191 include flexible gates 197, 198 that are mounted to traverse the central slot 199 between the front ends of the fork-like device 191. These gates 197, 198 exhibit variable resilient bias toward closure over the front end of the slot 199 that is easily overcome to admit the side-branch vessel 193 through the gates 197, 198 for captivation within the slot 199 upon forward movement of the device. However, the gates 197, 198 exhibit stiffer resilient bias perpendicular to the vessel 195 in order to retract the vessel 195 as the side-branch vessel 193 within the slot 199 is cauterized and transected.

Figure 28:
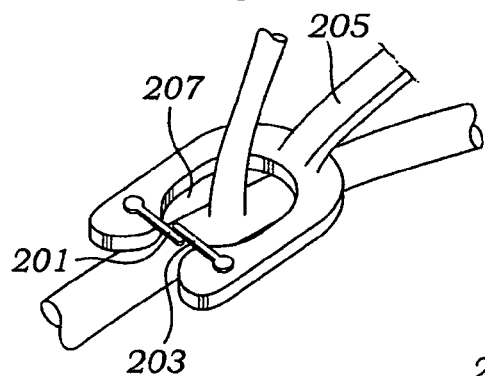
FIG. 28 is a partial perspective view of a vessel retractor according to another embodiment of the present invention.
Figure 29:
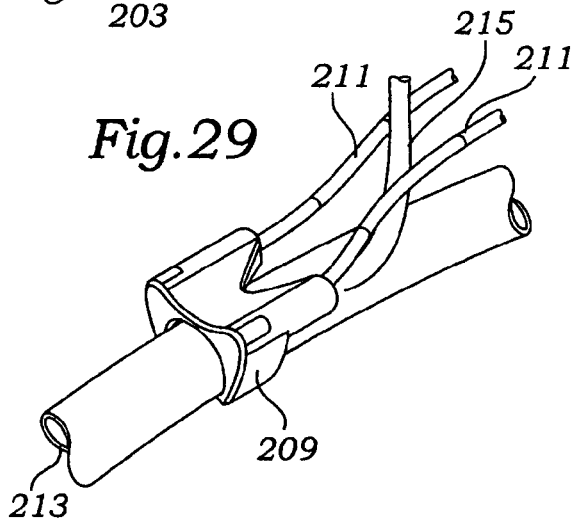
FIG. 29 is a partial perspective view of a vessel retractor according to another embodiment of the present invention.
Figure 30A:
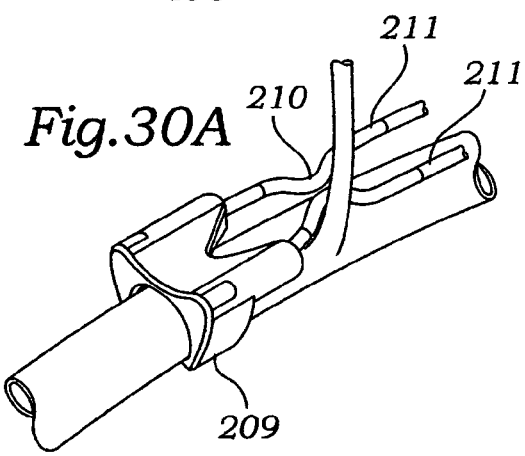
Figure 31:
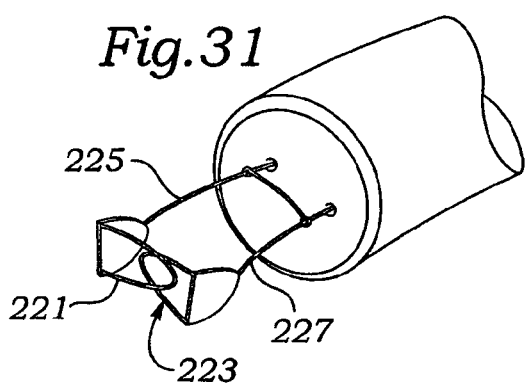
FIG. 31 is a partial perspective view of a vessel retractor according to another embodiment of the present invention.

In one embodiment, as illustrated in FIG. 28, the gates 201, 203 at the front end of the fork-like device 205 may be disposed on a top surface of the device near the forward end for pivotal movement in opening and closing to receive and captivate a side-branch vessel within the slot 207 of the device 205. Alternatively, as shown in FIG. 29, the fork-like device may be configured as a descending U-shaped retractor 209 supported on one or more resilient support wires 211. To facilitate placing the retractor 209 about the vessel 213 in proximity with a side-branch vessel 215, the support wires 211 may be configured in close proximity to a narrowed region 210 behind the retractor 209, as shown in FIGS. 30A and 30B, to diverge from parallel support wires or parallel-edged structure to facilitate convenient manipulation about intersections of side-branch vessels with the harvested vessel. In alternative embodiments of the invention, as illustrated in FIG. 31, the gates may be formed as thin wire loop 221, 223 attached to resilient wire supports 225, 227.

Figure 32:
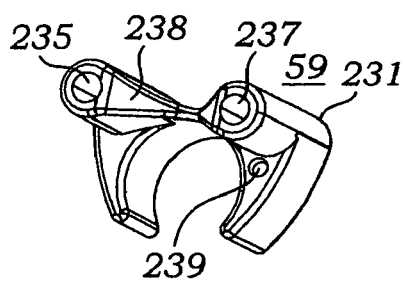
FIG. 32 is a perspective view of the vessel retractor of FIG. 8.

Referring now to FIG. 32, there is shown a perspective view of the inverted U-shaped vessel retractor 59 of FIG. 8 configured for attachment to one or more resilient supports. At least one such wire support 60, as shown in FIG. 8, attaches within bore 237, and a supporting hollow tube 61, as shown in FIG. 8, attaches within bore 235 that is channeled to an outlet orifice 238. This orifice serves as a nozzle for spraying liquid onto an adjacent lens of an endoscope, or for otherwise supplying liquid to a surgical site. An aperture 239 is provided in one leg of the retractor 231 for selectively positioning a suture loop about a vessel to be occluded and severed for harvesting from the body. Alternatively, a suture loop 8 may be manipulated relative to a vessel in a manner similar to the manner as previously described with references to FIG. 22. In this configuration, the vessel retractor may be deployed from the distal end of a supporting body under manual manipulation from a proximal end of such body.

Figure 33:
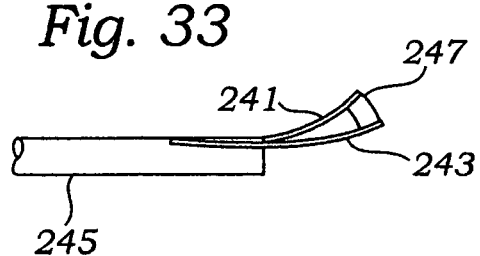
FIG. 33 is a partial perspective view of a vessel retractor in accordance with another embodiment of the present invention.

Referring now to FIG. 33, there is shown another embodiment of a vessel retractor including a pair of resilient support wires 241, 243 that are disposed to slide within the supporting body 245, and that support a flexible sling 247 therebetween near the distal ends thereof. In this configuration, a vessel may be contacted and retracted by the flexible sling 247 that is tensioned taut by the divergent orientation of the resilient support wires 241, 243. Upon slidable retraction of the support wires 241, 243 into the distal end of the supporting body 245, the flexible sling 247 is confined between the support wires 241, 243 that converge toward parallel orientation as retracted into the support body 245.

Control Members for Vessel Harvester.

Referring again to FIG. 8, and to FIGS. 34A-34I, there are shown the exploded and perspective views of the vessel harvester and associated components according to one embodiment of the present invention. The left half section 71 of the handle is shown inverted for clear illustration of internal structure. In this embodiment, the surgical effector devices described herein are manipulatable at the distal end of tool cannula 51 in response to manual manipulation of control members 63, 65 and 67 mounted in the handle of the device that is attached to the proximal end of the tool cannula 51. Specifically, the handle includes a rear bell-shaped section 73 that remains oriented in fixed axial alignment with a light post 16 of an endoscope 9 that is received in snap-fitting engagement within the side slot 74. This bell-shaped section 73 includes a rear aperture 78 that receives a conventional eye piece or camera attachment to an endoscope disposed within the section 73, and includes a front end 80 of the rear section 73.

Figure 34F:
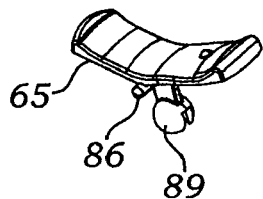
FIGS. 34A-34I are perspective views of components forming the vessel harvester of the embodiment illustrated in FIG. 8.
Figure 34A:
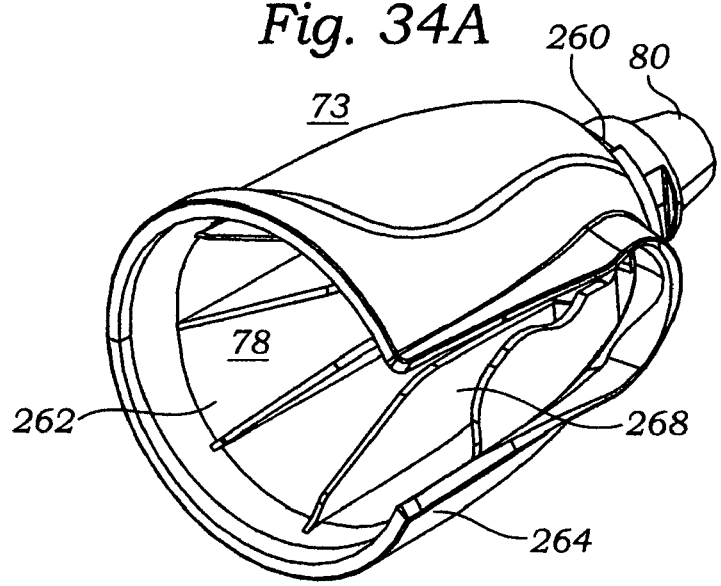
Figure 34D:
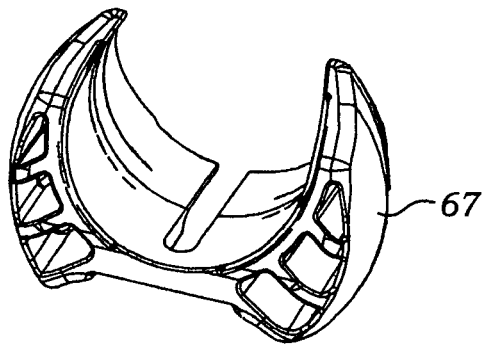
Figure 34E:
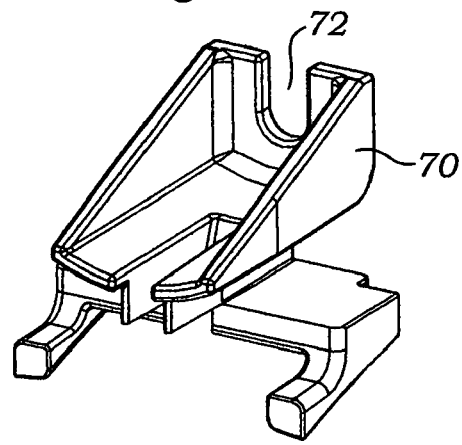
Figure 34B:
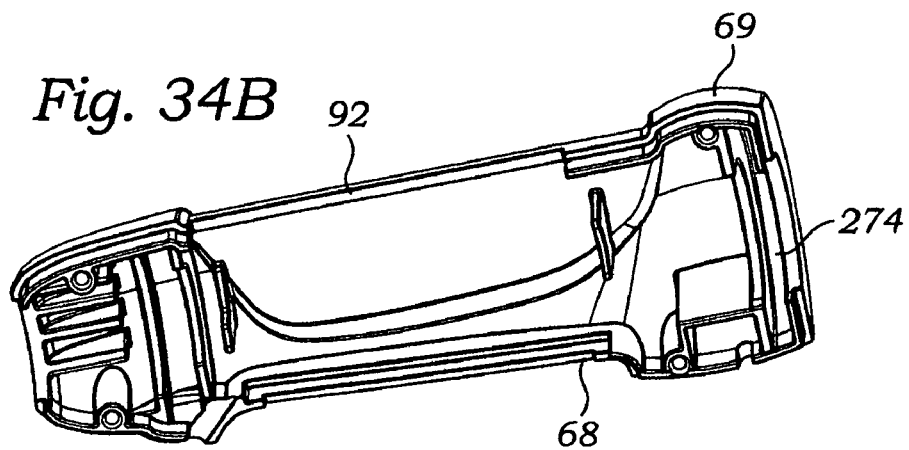

This rear section 73 rotatably attaches to left and right half sections 69, 71 of the forward section of the handle that are formed as shown in FIGS. 34A and 34B. Components, as later described herein, are assembled in the left half section 69, and the right half section 71 is then attached to complete the handle. In this configuration, the left and right half sections rotate about the bell-shaped rear section 73 which attaches at flange 260 disposed within annular groove 274. The half sections 69, 71 slidably support the control member 67 shown in FIG. 34D which, in turn, supports thereon a pivot carriage 70 shown in FIG. 34E that links to the outer sheath 79 of the bipolar scissors 81. The slot 76 near the proximal end of the outer sheath 79 slides into and is captivated within the slot 72 in pivot carriage 70. Thus, sliding the control member 67 back and forth axially along the longitudinal slot 68 shown in FIG. 34B formed in the left and right half sections 69, 71 retracts and deploys the scissor assembly 81 relative to the distal end of tool cannula 51.

The pivot carriage 70 illustrated in FIG. 34E supports a rocking lever 65 shown in FIG. 34F on integral pivot shaft 86 that is oriented laterally to the direction of slidable movement of the control member 67. The rocking lever 65 includes a lever arm 89 that engages the rods 75, 77 shown in FIG. 8 which extend from the proximal end of the sheath 79 of the scissor assembly. Thus, rocking the lever 65 about its pivot shaft 86 linked in this manner to the scissor blades 81 causes the blades to open and close in scissor-like motion.

Figure 34C:
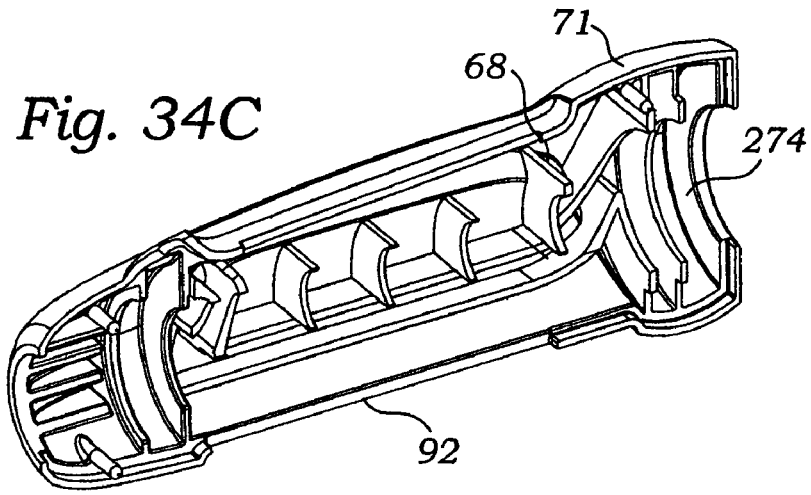
Figure 34H:
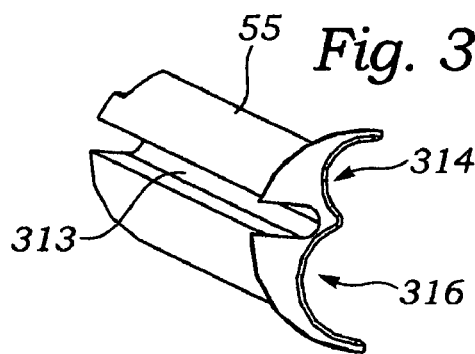
Figure 34G:
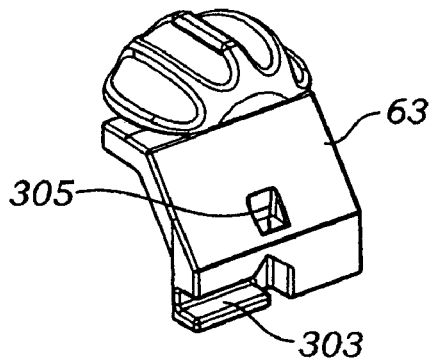

The left and right half sections 69, 71 of the handle also slidably support a control member 63 shown in FIG. 34G for movement back and forth in the longitudinal slot 92 shown in FIGS. 34B and 34C formed in the left and right half sections 69, 71. The control member couples to the activating rod 61 shown in FIG. 8 of the vein retractor 59 via the angled end 294 that engages within the groove 303 and aperture 305 shown in FIG. 34G. Thus, sliding the control member 63 back and forth within the slot 92 retracts and deploys the vessel retractor 59 from the distal end of the tool cannula 51.

Figure 34I:
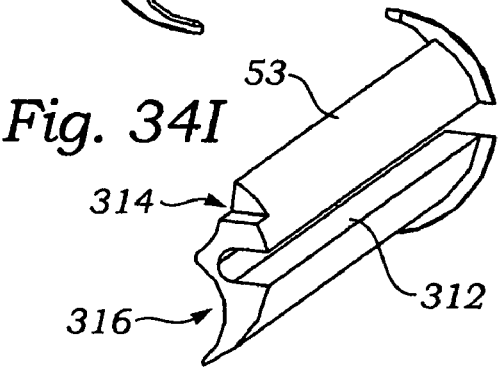

The sheath 79 shown in FIG. 8 supporting the scissor assembly 81 slides within the lumen 314 shown in FIG. 34H that is formed in right and left half inserts 53, 55 shown in FIGS. 34H and 34I. In addition, an endoscope is slidably supported within the lumen 316 that is formed by the inserts 53, 55, and the rod and tube 60, 61 shown in FIG. 8 that support the vessel retractor 59 and are slidably supported within the outer grooves 312, 313 formed within the left and right inserts 53, 55.

Figure 35:
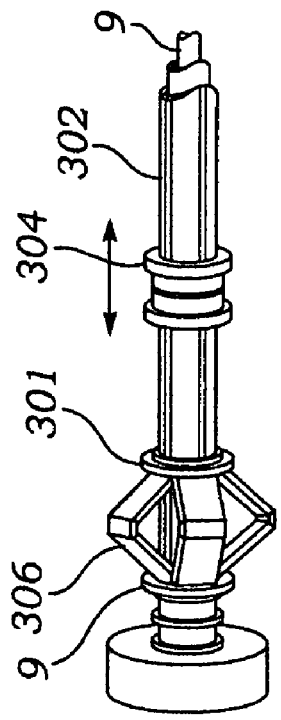
FIG. 35 is a frontal view of another embodiment of control members for a vessel harvester in accordance with the present invention.

Referring now to FIG. 35, there is shown another embodiment of the control members mounted at the proximal end of the tool cannula 51 for manipulating surgical effector devices at the distal end thereof. Specifically, in this embodiment one or more coaxial sheaths 301, 302 are disposed about the endoscope 9 to facilitate axial or orbital rotation of the surgical effector devices relative to the axis and orientation of the endoscope 9. The ring 304 on sheath 302 may be slid axially to deploy and retract the vessel retractor at the distal end of the sheath 302, and the axial compression assembly 306 is linked to the scissors mounted at the distal end of the sheath 301 for deployment and retraction thereof by squeezing or releasing assembly 306. Forward sliding movement of the axial compression assembly 306 deploys the scissors, and relative axial compression of the forward and rearward components of the compression assembly 306 actuate the scissor blades in any selected angular orientation about the endoscope 9 to facilitate transecting side-branch vessels encountered lying in any orientation relative to the vessel that is to be harvested.

Figure 36:
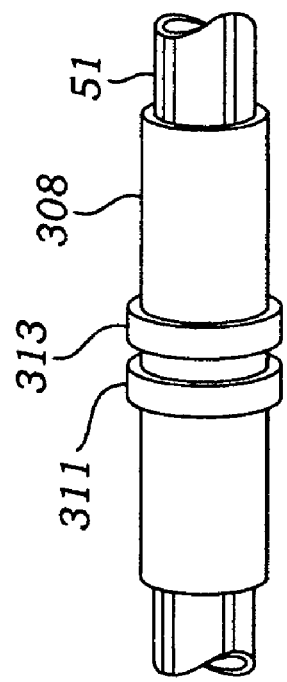
FIG. 36 is a frontal view of another embodiment of control members for a vessel harvester in accordance with the present invention.

Referring now to FIG. 36, there is shown another embodiment of control members disposed at the proximal end of tool cannula 51 for manually manipulating at the distal end thereof the selected surgical effector devices that are linked to the control members. Specifically, the control member 308 slides forward toward the distal end of the tool cannula 51, for example, to deploy the vessel retractor from the distal end of the tool cannula 51. And, separately slidable rings 311, 313 are supported on the tool cannula 51 and are linked, for example, to scissors at the distal end of the tool cannula 51 to deploy and retract the scissors in response to sliding the rings 311, 313 together, and to operate the scissors to transect tissue in response, for example, to sliding movement of the proximal ring 311 proximally relative to ring 313 in order to close the scissor blades.

Referring now to FIG. 37 there is shown an exploded perspective side view of the package of components suitable for use in harvesting a vessel from a patient's body. Specifically, a pre-formed container 332 includes a lower tray 334 having a peripheral ridge 335 about its upper surface, and an upper lid 336 for closing the tray 334 having a recess 338 in the peripheral flange that conforms to the ridge 336 for forming a seal at least against particulates from intruding into the confined volume between the tray 334 and lid 336. The tray 334 includes an elongated recess 340 along a portion of the bottom that is elevated to a mid-height level for receiving the tool cannula 51 therein. The elevated bottom includes one or more recesses 342, 344 for confining a number of dissecting tips 11 of different configurations, for use as previously described herein, and a syringe 341 for attachment to the fluid connector 66 shown in FIG. 8 for delivering fluid under pressure to wash the endoscope lens, as previously described herein. The remaining, unelevated portions of the bottom of the tray 334 provide internal space for the handle assembly 69, 71, 73, and to provide exterior supports 352, 354, or pods, on which the tray 334 may stably rest. The upper lid 336 includes a depression 356 that descends closely to the elevated portion of the bottom at mid-height level that includes the recesses 340, 342, 344 for retaining the components previously described herein in the respective recesses. This entire structure 332 may be vacuum formed of thermoplastic sheet material such as PTFE or PETE polymers. The components of the container 332 and the surgical components housed in the container may be substantially assembled as shown for sterilization processing and sealing within an outer envelope 358 of thin flexible impervious plastic material of the types, for example, as previously described above.

The sterilized components within the sealed envelope 358 are disposed within an external carton 360 that provides additional protection from damage during shipping and handling. In addition, the carton 360 contains another sealed envelope 362 in the region beneath the elevated bottom portion of the tray 334. This sealed envelope 362 contains a surgical access port of the type, for example, as illustrated and described in pending U.S. patent application Ser. No. 09/648,660, entitled "Endoscopic Surgical Access Port and Method", filed on Aug. 25, 2000 by P. Callas et al. Such surgical access port includes a blunt-tip hollow trocar that facilitates operation of the dissecting endoscope 9 and tool cannula 51 within insufflated surgical environments, and that may therefore be included in the packaging discussed above for the convenience of a surgeon having the components available with which to perform a vessel-harvesting procedure.

Figure 38A:
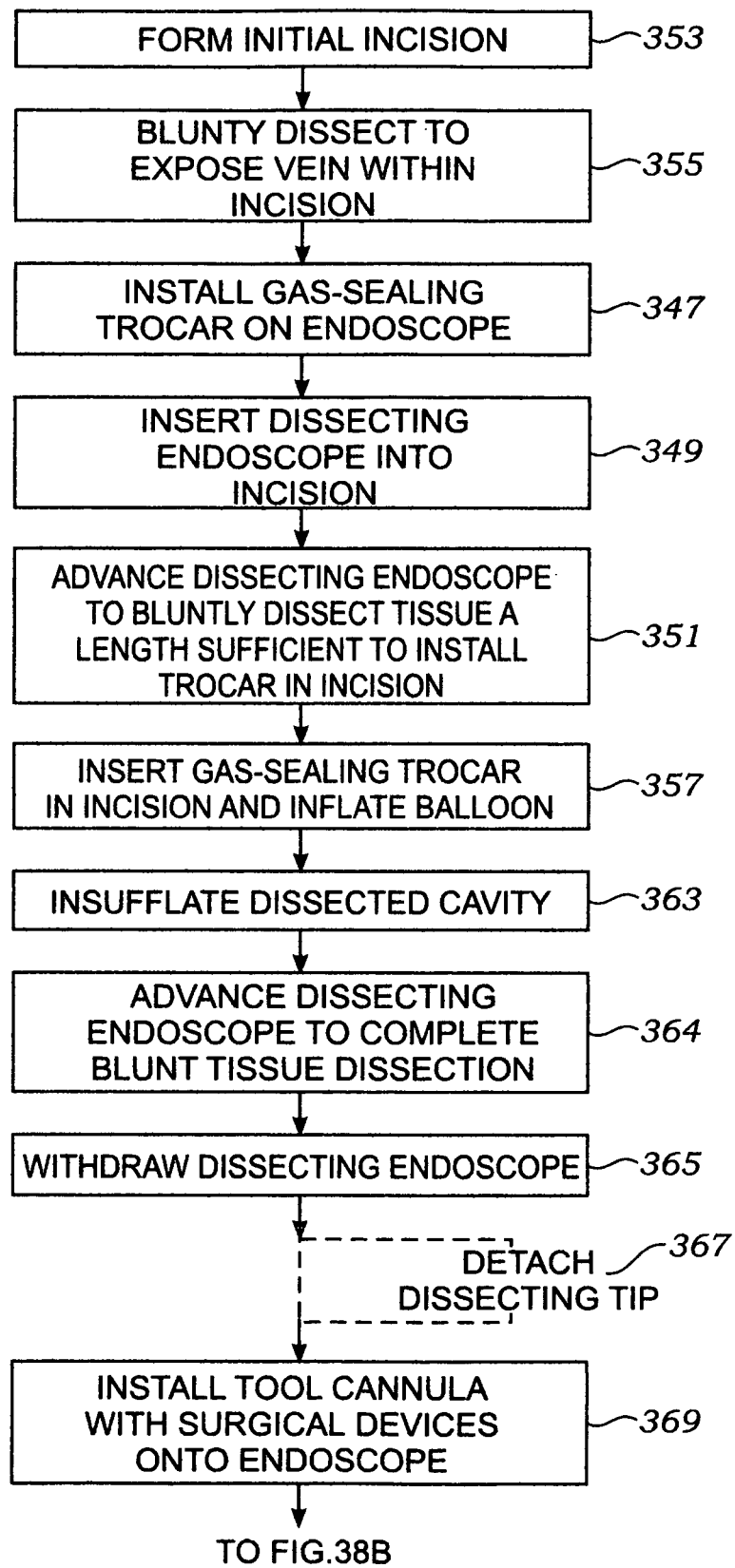

In general, with reference to the flow chart of FIGS. 38A and 38B, the rigid dissecting endoscope 9 as illustrated in FIG. 1B may be inserted through a seal 347 that is affixed to an outer, hollow barrel of a gas-sealing trocar of a type, for example, as disclosed in aforementioned U.S. patent application Ser. No. 09/648,660. Thus, tissue dissection under insufflation may be accomplished 364 along the vessel to be harvested using the elongated dissecting endoscope 9 inserted through the sliding gas seal, and fitted with a blunt tissue-dissecting transparent tapered tip 11. Connecting tissue may be dissected away from the vessel being harvested, under visualization through the tip 11, in response to manual manipulation of the proximal end of the endoscope 9 that advances the tip 11 and optional tissue dilator 13 through tissue surrounding the vessel along the course thereof.

Following such tissue dissection to form an anatomical space or cavity along a segment of the vessel, the endoscope 9 may be withdrawn 365 from such cavity through the sliding gas seal of the hollow trocar, and may then be reconfigured by detaching 367 the tapered tip 11, and by sliding 369 over the length of the endoscope 9 the overlying tool cannula 51 that carries the surgical effector devices including the retractor 59 and scissors 81, as previously described. The tapered, transparent tip 11 may optionally be retained on the viewing, distal end of the endoscope 9 and overlayed by the tool cannula 51 that slides into place over the length of the endoscope 9, or alternatively that attaches contiguously and eccentrically to the endoscope, as previously described herein.

This configuration of tool cannula 51 overlaying or otherwise attached to the endoscope 9, may again be slidably inserted 371 through the resilient gas-seal of the hollow trocar to position the surgical effector devices mounted at the distal, open end of tool cannula 51 for retraction, cauterization and transecting of vessel structures encountered within the anatomical space previously formed by blunt tissue dissection along the course of the vessel being harvested. In one embodiment, for example, the dissection endoscope 9 may be supplied separately packaged for resterilization prior to each use. The cooperating components such as tips 11 and dilators 13, and one or more tool cannulas 51, each with a selected set of effector devices deployable and manipulatable at the distal end of the tool cannula 51, and (optionally) a gas-sealing hollow trocar are therefore supplied together for convenience in sterilized condition as packaged within respective hermetically-sealed envelopes 358, 362 and housed within carton 360. Thus, for each vein harvesting procedure there need only be supplied in a kit a trocar and a tool cannula 51 with its selected effector devices carried thereby, and selected effector devices for attachment to the dissection cannula, and a syringe 341 for performing a vessel harvesting operation with a reusable dissection endoscope 9.

Specifically, as illustrated in the flow chart of FIGS. 38A and 38B, the surgical apparatus of the present invention facilitates the surgical procedures for harvesting a vessel such as the saphenous vein from a patient. The surgical procedure includes forming an initial small incision 353 over the vessel such as the saphenous vein to permit a surgeon to bluntly dissect tissue 355 down to the adventitia layer and to expose the saphenous vein. When insufflation is indicated to inflate and expand the anatomical space to be formed along the vessel, then a blunt-tip trocar may be installed 347 on the dissecting endoscope 9 which is then inserted 349 into the initial incision and advanced along the vessel a sufficient distance to install 351 the hollow trocar in the incision. The hollow barrel of the trocar includes an inflatable balloon about the outer circumference of the distal end, and such balloon is inflated following insertion 357 of the trocar within the initial incision to anchor the trocar in gas-tight sealing orientation within the initial incision. Gas under pressure is then supplied through the trocar to insufflate 363 the dissected cavity.

The dissection endoscope 9, with the blunt tapered transparent tip 11 attached to the distal end thereof and with the shaft of the dissecting endoscope disposed within the sliding gas seal and through the inner bore of the trocar, is now advanced 364 along the vessel to complete the blunt tissue dissection along the vessel while visualizing the tissue dissection through the transparent tip 11 at the distal end of the dissection endoscope 9. The blunt dissection of connecting tissue away from the saphenous vein and around tributary vessels may proceed on anterior and posterior sides of the vein along the course of the vein to the full extent or length of the dissecting endoscope 9 by manual manipulation of the proximal end thereof that protrudes from the sliding gas seal of the trocar. Tissue dissection can be assisted by palpating tissue through skin in known manner in order to manipulate tissue toward and around the tip 11.

Upon completion of tissue dissection with the dissecting endoscope 9 along the course of the vessel, in one or opposite directions from the initial incision, the dissecting endoscope 9 is withdrawn 365 from the cavity through the sliding gas seal of the trocar, and the blunt dissecting tip 11 may be detached 367 from (or alternatively retained on) the distal end of the endoscope 9 to accommodate reconfiguration of the endoscope for the next phase of the vessel-harvesting procedure. Specifically, with the tip 11 (and optional dilator 13) removed from the distal end of the dissection endoscope 9, the overlying tool cannula 51 may be slid onto the distal end and full length of the dissection endoscope 9 (or other scope) to equip the endoscope 369 with, for example, a set of surgical effector devices such as a vein retractor 59 and bipolar scissors 81 needed to prepare the lateral or side-branch vessels for transection from the vessel to be harvested. In an alternative configuration, the transparent tip 11 may remain attached to the distal end of the endoscope as reconfigured with the overlying or adjacent eccentric cannula, as previously described herein.

The endoscope 9 and tool cannula 51 with associated retractor 59 and scissors 81 recessed within the open distal end of the tool cannula 51 is inserted 371 through the sliding gas seal of the trocar into the insufflated cavity. Under visualization through the endoscope 9, each lateral or side-branch vessel that is encountered along the course of the saphenous vein is cauterized using bipolar electrodes disposed on the blades of scissors 81, as selectively deployed from the open distal end of the tool cannula 51, and is transected by the scissors 81 in conventional manner using the control members 65 and 67 in the handle at the proximal end of the tool cannula 51 to operate the scissor blades 81. Of course, other surgical effector devices such as ligating and transecting instruments, vessel retractor, endoscope washer, RF-energized or ultrasonic or thermally-hot cauterizer, and the like may be supported by the tool cannula 51 for selective deployment from the open distal end of the tool cannula 51, as previously described herein. The retractor 59 on shaft 60 may be deployed from the open end of the tool cannula 51 and positioned about the vessel to laterally displace or retract its position 373 relative to a side branch that is to be cauterized and transected using the bipolar scissors 81.

After all side branches encountered along the segment of the vessel that is isolated within the insufflated cavity have been ligated, cauterized and transected, the vessel may be occluded and severed in conventional manner at the remote ends of the desired segment for removal 375 from the cavity, for example, through the initial incision.

Figure 39A:
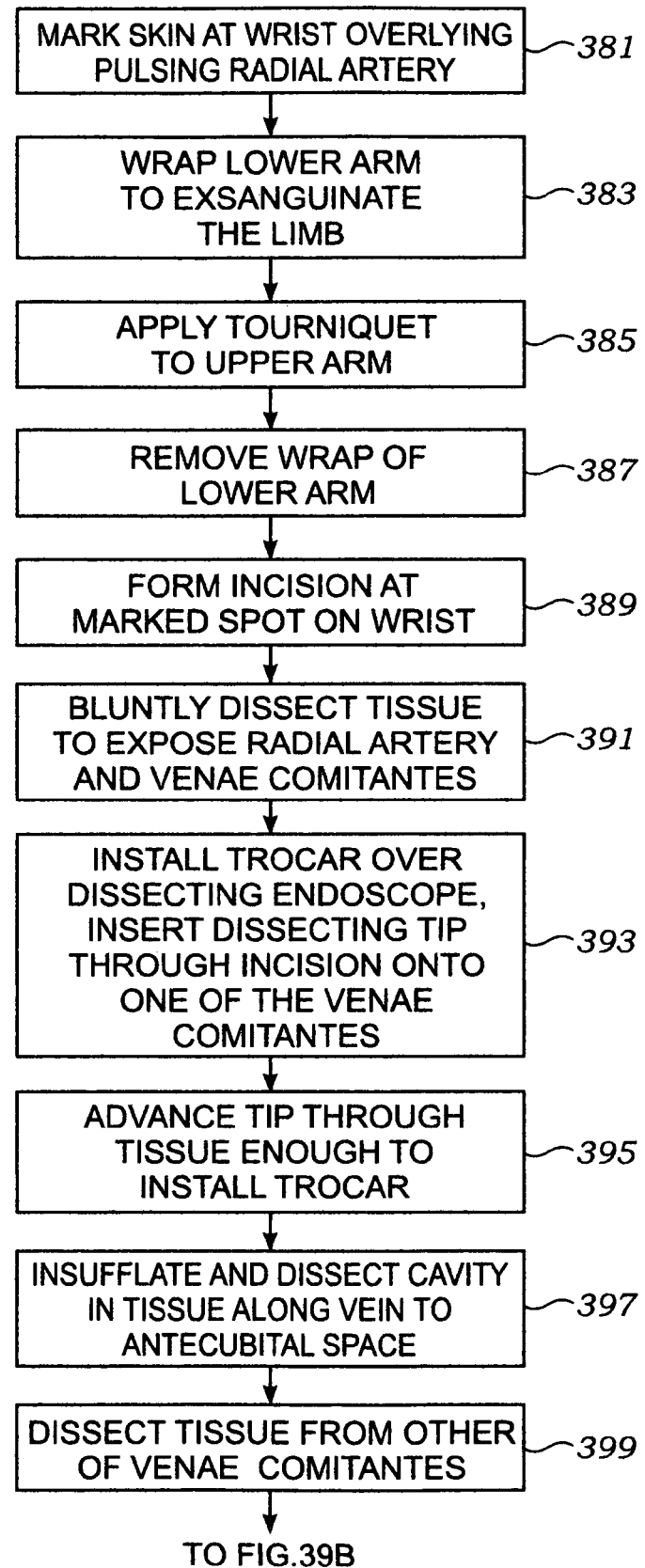
FIGS. 39A and 39B comprise a flow chart illustrating a procedure for harvesting the radial artery in accordance with the present invention.
Figure 39B:
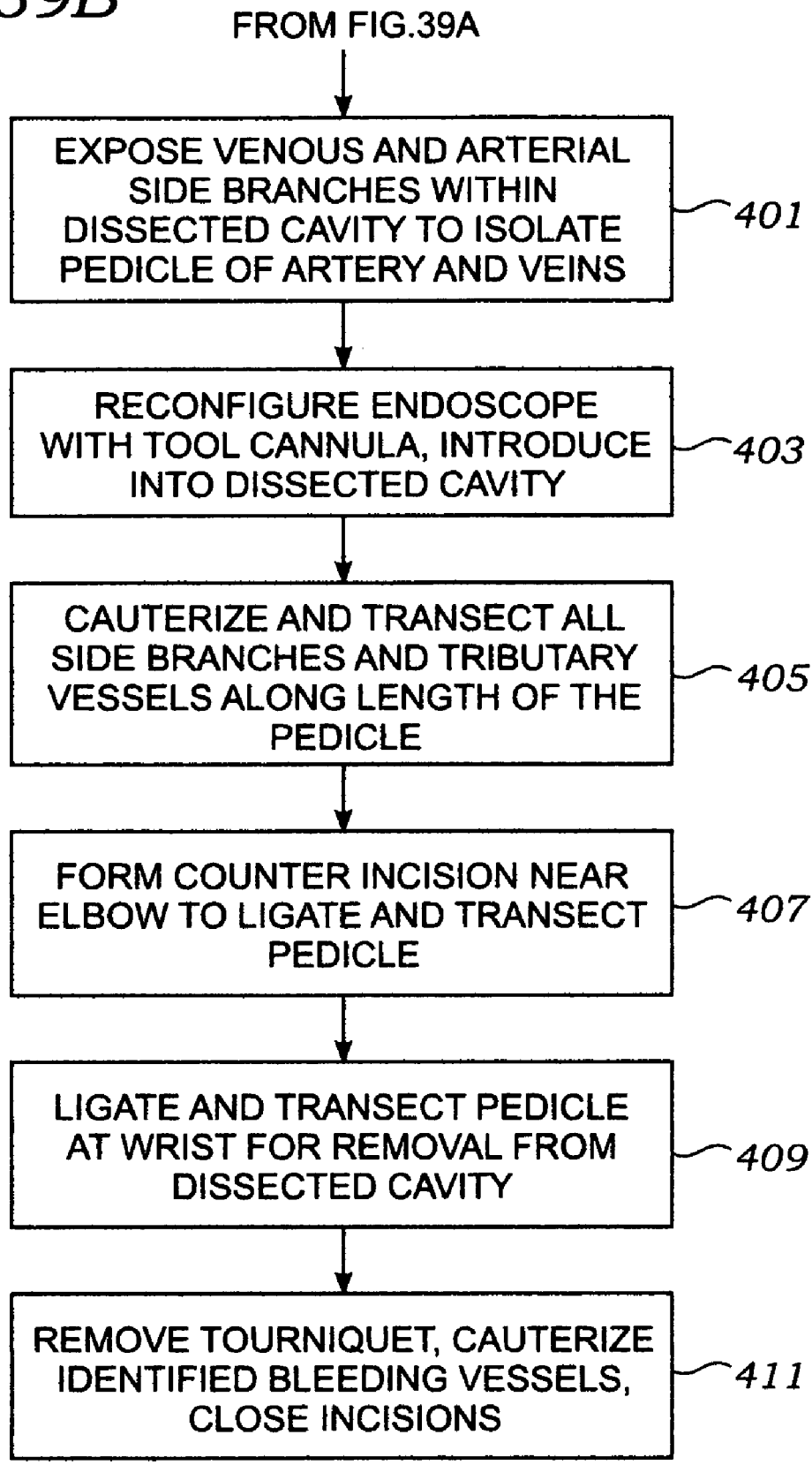

As illustrated in the flow chart of FIGS. 39A and 39B, the surgical apparatus of the present invention also facilitates the surgical procedures for harvesting a vessel such as the radial artery from a patient. Specifically, the surgical procedure includes marking the skin at the wrist 381 overlying the pulse of the radial artery, as illustrated in FIG. 1A. The lower arm is wrapped 383 with an elastic band such as an Esmarch bandage to force blood out of the lower arm. An inflatable tourniquet is then applied 385 to the upper arm to preserve the bloodless condition of the lower arm. The Esmarch bandage is removed 387 and an incision is made 389 in the wrist at the spot previously marked to indicate the location of the radial artery. Metzenbaum scissors are used to bluntly dissect tissue 391 within the incision to expose the radial artery and the adjacent venae comitantes veins.

A hollow short trocar is disposed over the dissecting endoscope, and the tapered tip is inserted through the incision 393 onto the anterior aspect of one of the veins lying adjacent to the radial artery. The dissecting tip is advanced sufficiently far along the vein to allow a balloon on the exterior surface of the trocar to be inflated into gas-sealing position within the incision 395. Gas under pressure is supplied through the trocar to insufflate the lower arm as the dissecting endoscope is advanced 397 through tissue along the course of the vein to the antecubital space about the elbow. The tip of the dissecting endoscope is pulled back to the trocar and is advanced along the posterior aspect of the vein. Then, tissue dissection is similarly performed on the adjacent vein 397, and the tip of the dissecting endoscope is then used to expose 401 venous and arterial side branches along the length of the dissected cavity until a pedicle of the radial artery and the paired venae comitantes has been isolated. The dissecting endoscope is then removed from the dissected cavity, and is reconfigured with the overlying or adjacent tool cannula, as previously described herein, for reintroduction 403 through the trocar into the dissected and insufflated cavity. The isolated veinous and arterial side branches and tributaries are then cauterized and transected along the length of the isolated pedicle 405 in a manner as previously described herein, commencing with such side branches and tributaries nearest the wrist and progressing toward the elbow. A counter incision is performed at the elbow and the pedicle of radial artery and paired veins is ligated with a suture and is transected 407. The pedicle is similarly ligated and transected at the wrist 409 for removal of the pedicle from the dissected cavity. The tourniquet is then removed, and any bleeding vessels are cauterized and the incision closed to complete the harvesting 411 of the segment of the radial artery from the lower arm.

Therefore, the apparatus and method according to the present invention improve the surgical procedures for harvesting a vessel from a patient with reduced trauma to the patient. The convenient operability of a reconfigurable dissection endoscope and associated tool cannula as a support at the distal end thereof for various surgical effector devices greatly facilitate the surgical procedures for preparing the vessel in situ for removal from the body.

What is claimed is:

1. A tissue dissector, comprising:
   an elongated tubular body having a central axis extending between a proximal end and a distal end and enclosing an endoscopic imaging element; and
   a dissecting, viewing and dilating unit removably mounted on the distal end of the tubular body, including:
   a transparent distal tip having substantially conical tapered outer walls converging distally with conical symmetry about the central axis from a cylindrical diameter to a blunt end for dissecting tissue, the tip being disposed on a distal end of the body to dissect tissue and facilitate passage of the tubular body through tissue under visualization through the tip by the endoscopic imaging element; and
   a non-inflatable dilating element spaced proximally a selected length away from the cylindrical diameter of the distal tip and having an exterior contour that is disposed with rotational symmetry about the central axis and that gradually increases in cross-sectional dimension symmetrically about the central axis in the proximal direction from a distal edge of the dilating element that is spaced the selected length from the cylindrical diameter of the distal tip to a maximum cross-sectional dimension greater than the cross-sectional dimension of said distal edge, the dilating element then decreasing in cross-sectional dimension symmetrically about the central axis in the proximal direction to a cylindrical diameter smaller than said maximum cross-sectional dimension at a proximal edge for facilitating atraumatic expansion of tissue following dissection by the tapered distal tip during advance of the tissue dissector through tissue, said selected length of spacing having an outer-dimension less than the maximum cross-sectional dimension of the dilating element and positioning the dilating element within an angle of the symmetrically conical tapered outer walls of the tip to inhibit the dilating element from impeding contact of the outer walls of the tip with a target vessel.

2. The tissue dissector of claim 1, wherein the distal tip and the dilating element spaced the selected length from the distal tip are formed as a single unit removably mounted on the tubular body substantially symmetrically about the central axis.

3. The tissue dissector of claim 1 in which the dilating element is resiliently compressible in cross-sectional dimensions.

* * * * *